(12) United States Patent
Friend et al.

(10) Patent No.: US 7,130,746 B2
(45) Date of Patent: Oct. 31, 2006

(54) COMPUTER SYSTEMS AND COMPUTER PROGRAMS FOR DETERMINING PROTEIN ACTIVITY LEVELS USING GENE EXPRESSION PROFILES

(75) Inventors: Stephen H. Friend, Seattle, WA (US); Roland Stoughton, San Diego, CA (US)

(73) Assignee: Rosetta Inpharmatics LLC, Seattle, WA (US)

( * ) Notice: Subject to any disclaimer, the term of this patent is extended or adjusted under 35 U.S.C. 154(b) by 510 days.

(21) Appl. No.: 09/975,843

(22) Filed: Oct. 12, 2001

(65) Prior Publication Data

US 2002/0045197 A1 Apr. 18, 2002

Related U.S. Application Data

(62) Division of application No. 09/303,082, filed on Apr. 30, 1999, now Pat. No. 6,324,479.

(60) Provisional application No. 60/090,046, filed on Jun. 19, 1998, provisional application No. 60/084,742, filed on May 8, 1998.

(51) Int. Cl.
  *G01N 33/48* (2006.01)
  *G06F 19/00* (2006.01)
  *G06G 7/48* (2006.01)

(52) U.S. Cl. ............... 702/19; 702/20; 703/20

(58) Field of Classification Search ............ 702/19, 702/20; 703/11; 435/4, 6, 7.2
  See application file for complete search history.

(56) References Cited

U.S. PATENT DOCUMENTS

| | | | |
|---|---|---|---|
| 4,537,861 A | 8/1985 | Elings et al. | |
| 4,946,778 A | 8/1990 | Ladner et al. | |
| 5,510,270 A | 4/1996 | Fodor et al. | |
| 5,539,083 A | 7/1996 | Cook et al. | |
| 5,556,752 A | 9/1996 | Lockhart et al. | |
| 5,569,588 A | 10/1996 | Ashby et al. | |
| 5,578,832 A | 11/1996 | Trulson et al. | |
| 5,604,115 A | 2/1997 | Sladek et al. | |
| 5,716,622 A | 2/1998 | Darnell, Jr. et al. | |
| 5,965,352 A | 10/1999 | Stoughton et al. | |
| 6,024,983 A * | 2/2000 | Tice et al. | 424/501 |
| 6,132,969 A | 10/2000 | Stoughton et al. | |

FOREIGN PATENT DOCUMENTS

| | | |
|---|---|---|
| EP | 0 534 858 A1 | 9/1992 |
| WO | WO 88/09810 | 12/1988 |
| WO | WO 90/11364 | 10/1990 |
| WO | WO 96/23078 | 8/1996 |
| WO | WO 97/27560 | 7/1997 |
| WO | WO 97/29212 | 8/1997 |
| WO | WO 98/06874 | 2/1998 |
| WO | WO 98/41531 | 9/1998 |
| WO | WO 99/05323 | 2/1999 |

OTHER PUBLICATIONS

U.S. Appl. No. 09/303,082, filed Apr. 30, 1999, Friend et al.
Anderson et al., 1994, "Involvement of the protein tyrosine kinase p56lck in T cell signaling and thymocyte development", Adv Immunol 56:151-178.
Belshaw et al., 1996, "Controlling protein association and subcellular localization with a synthetic ligand that induces heterodimerization of proteins", Proc Natl Acad Sci USA 93:4604-4607.
Benoist and Chambon, 1981, "In vivo sequence requirements of the SV40 early promoter region", Nature 290:304-310.
Biocca and Cattaneo, 1995, "Intracellular immunization: antibody targeting to subcellular compartments", Trends Cell Biology 5:248-252.
Blanchard and Hood, 1996, "Sequence to array: probing the genome's secrets", Nat Biotechnol 14:1649.
Blanchard and Hood, 1996, "High-density oligonucleotide arrays", Biosensors and Bioelectronics 11:687-690.
Bradbury et al., 1995, "The cloning of Hybridoma V regions for their ectopic expression in intracellular and intercellular immunization" in *Antibody Engineering*, vol. 2, Borrebaeck (ed.) Oxford University Press, pp. 295-361.
Brinster et al., 1982, "Regulation of metallothionein—thymidine kinase fusion plasmids injected into mouse eggs", Nature 296:39-42.
Brown and Hartwell, 1998, "Genomics and human disease-variations on variation", Nature Genetics 18:91-93.
Burke and Warren, 1984, "Microinjection of mRNA coding for an anti-Golgi antibody inhibits intracellular transport for a viral membrane protein", Cell 36:847-858.

(Continued)

*Primary Examiner*—Andrew Wang
*Assistant Examiner*—Anna Skibinsky
(74) *Attorney, Agent, or Firm*—Jones Day

(57) ABSTRACT

The present invention provides methods for determining the level of protein activity in a cell by: (i) measuring abundances of cellular constituents in a cell in which the activity of a specific protein is to be determined so that a diagnostic profile is thus obtained; (ii) measuring abundances of cellular constituents that occur in a cell in response to perturbations in the activity of said protein to obtain response profiles and interpolating said response profiles to generate response curves; and (iii) determining a protein activity level at which the response profile extracted from the response curves best fits the measured diagnostic profile, according to some objective measure. In alternative embodiments, the present invention also provides methods for identifying individuals having genetic mutations or polymorphisms that disrupt protein activity, and methods for identifying drug activity in vivo by determining the activity levels of proteins which interact with said drugs.

14 Claims, 5 Drawing Sheets

OTHER PUBLICATIONS

Burnette, 1981, "Western blotting: electrophoretic transfer of proteins from sodium dodecyl sulphate-polyacrylamide gels to unmodifed nitrocellulose and radiographic detection with antibody and radioiodinated protein A", A. Anal. Biochem. 112:195-203.

Bussey H et al., "The nucleotide sequence of chromosome I from *Saccharomyces cerevisiae*", Proc Natl Acad Sci U S A. Apr. 25, 1995;92(9):3809-13.

Cannon-Albright and Skolnick, 1996, "The genetics of familial breast cancer", Seminars in Oncology 23:1-5.

Cech, 1987, "The chemistry of self-splicing RNA and RNA enzymes", Science 236:1532-1539.

Chirgwin et al., 1979, "Isolation of biologically active ribonucleic acid from sources enriched in ribonuclease", Biochemistry 18:5294-5299.

Chowdhury et al., 1997, "Lack of association of angiotensin II Type 1 receptor gene polymorphism with diabetic neuropathy in insulin-dependant Diabetes mellitus", Diabet. Med. 14:837-840.

Cole et al., 1985, "The EBV-Hybridoma technique and its application to human lung cancer" in Monoclonal Antibodies and Cancer Therapy, Alan R. Liss, Inc., pp. 77-96.

Cote et al., 1983, "Generation of human monoclonal antibodies reactive with cellular antigens", Proc Natl Acad Sci USA 80:2026-2030.

Cotten and Birnstiel, 1989, "Ribozyme mediated destruction of RNA in vivo", EMBO J 8:3861-3866.

Cunningham and Dunlop, 1996, "Molecular genetic basis of colorectal cancer susceptibility", British Journal of Surgery 83:321-329.

Cyert et al., 1992, "Regulatory subunit (CNB1 gene product) of yeast Ca2+/calmodulin-dependent phosphoprotein phosphatases is required for adaptation to pheromone", Mol. Cell. Biol. 12:3460-3469.

DeRisi et al., 1996, "Use of a cDNA microarray to analyse gene expression patterns in human cancer", Nat Genet 14:457-460.

Deshaies et al., 1988, "A subfamily of stress proteins facilitates translocation of secretory and mitochondrial precursor polypeptides", Nature 332:800-805.

Dohmen et al., 1994, "Heat-inducible degron: a method for constructing temperature-sensitive mutants", Science 263:1273-1276.

Duez et al., 1991, "Use of an amoeba-proteus model for in-vitro cytotoxicity testing in phytochemical resarch application to euphorbia-hirta extracts", J. Enthnopharmacol., 34: 235-246.

Dujon B et al., "Complete DNA sequence of yeast chromosome XI", Nature. Jun. 2, 1994;369(6479):371-8.

Egholm et al., 1993, "PNA hybridizes to complementary oligonucleotides obeying the Watson-Crick hydrogen-bonding rules", Nature 365:566-568.

Feldmann H et al., "Complete DNA sequence of yeast chromosome II", EMBO J. Dec. 15, 1994;13(24):5795-809.

Ferguson et al., 1996, "A fiber-optic DNA biosensor microarray for the analysis of gene expression", Nature Biotechnol 14:1681-1684.

Fodor et al., 1991, "Light-directed, spatially addressable parallel chemical synthesis", Science 251:767-773.

Frebourg and Friend, 1992, "Cancer risks for germline p53 mutations", J. Clin. Invest. 90:1637-1641.

Friend, 1994,"p53: A glimpse at the puppet behind the shadow play", Science 265:334-335.

Froehler et al., 1986, "Synthesis of DNA via deoxynucleoside H-phosphonate intermediates", Nucleic Acids Res 14:5399-5407.

Galibert F et al., "Complete nucleotide sequence of *Saccharomyces cerevisiae* chromosome X", EMBO J. May 1, 1996;15(9):2031-49.

Gari et al., 1997, "A set of vectors with a tetracycline-regulatable promoter system for modulated gene expression in *Saccharomyces cerevisiae*", Yeast 13:837-848.

Gautier et al., 1987, "Alpha-DNA. IV: Alpha-anomeric and beta-anomeric tetrathymidylates covalently linked to intercalating oxazolopyridocarbazole. Synthesis, physicochemical properties and poly (rA) binding", Nucleic Acids Res 15:6625-6641.

Gibson, 1996, "Antisense approaches to the gene therapy of cancer—'Recnac' ", Cancer Metastasis Rev 15:287-299.

Goffeau et al., 1996, "Life with 6000 genes", Science 274:546, 563-567.

Good et al., 1997, "Expression of small, therapeutic RNAs in human cell nuclei", Gene Ther 4:45-54.

Gossen and Bujard, 1995, "Tight control of gene expression in mammalian cells by tetracycline-responsive promoters", Proc Natl Acad Sci USA 89:5547-5551.

Grassi and Marini, 1996, "Ribozymes: structure, function and potential therapy for dominant genetic disorders", Annals Medicine 28: 499-510.

Griffiths et al., 1994, "Isolation of high affinity human antibodies directly from large synthetic repertoires", EMBO J 13:3245-3260.

Haluska and Hodi, 1998, "Molecular genetics of familial cutaneous melanoma", Journal of Clinical Oncology 16:670-682.

Hanke et al., 1996, "Discovery of a novel, potent, and Src family-selective tyrosine kinase inhibitor. Study of Lck- and FynT-dependent T cell activation", J Biol Chem 271:695-701.

Haseloff and Gerlach, 1988, "Simple RNA enzymes with new and highly specific endoribonuclease activities", Nature 334:585-591.

Hayden et al., 1997, "Antibody engineering", Curr Opin Immunol 9:210-221.

Heller et al., 1997, "Discovery and analysis of inflammatory disease-related genes using cDNA microarrays", Proc. Natl. Acad. Sci. USA, 94: 2150-2155.

Herskowitz, 1987, "Functional inactivation of genes by dominant negative mutations", Nature 329:219-222.

Hoffmann et al., 1997, "A novel tetracycline-dependent expression vector with low basal expression and potent regulatory properties in various mammalian cell lines.", Nucleic Acids Res 25:1078-1079.

Hofmann A et al., 1996, "Rapid retroviral delivery of tetracycline-inducible genes in a single autoregulatory cassette", Proc Natl Acad Sci U S A.. May 28;93(11):5185-90.

Huse et al., 1989, "Generation of a large combinatorial library of the immunoglobulin repertoire in phage lambda", Science 246:1275-1281.

Inoue et al., 1987, "Sequence-dependent hydrolysis of RNA using modified oligonucleotide splints and RNase H", FEBS Lett 215:327-330.

Inoue et al., 1987, "Synthesis and hybridization studies on two complementary nona(2'-O-methyl)ribonucleotides", Nucleic Acids Res 15:6131-6148.

Johnston M et al., "Complete nucleotide sequence of *Saccharomyces cerevisiae* chromosome VIII", Science. Sep. 30, 1994;265(5181):2077-82.

Johnston and Davis, 1984, "Sequences that regulate the divergent GAL1-GAL10 promoter in *Saccharomyces cerevisiae*", Mol Cell Biol 8:1440-1448.

Kerjan et al., 1986, "Nucleotide sequence of the *Saccharomyces cerevisiae* MET25 gene", Nucleic Acids Res 14:7861-7871.

Kohler and Milstein, 1975, "Continuous cultures of fused cells secreting antibody of predefined specificity", Nature 256:495-497.

Koizumi et al., 1988, "Construction of a series of several self-cleaving RNA duplexes using synthetic 21-mers", FEBS Lett 228:228-230.

Koizumi et al., 1988, "Cleavage of specific sites of RNA by designed ribozymes", FEBS Lett 239:285-288.

Kozbor and Roder, 1983, "The production of monoclonal antibodies from human lymphocytes", Immunol Today 4:72.

Krug and Berger, 1987, "First-strand cDNA synthesis primed with oligo(dT)", Methods Enzymol 152:316-325.

Lander, 1996, "The new genomics: global views of biology", Science 274:536-539.

Letsinger et al., 1989, "Cholesteryl-conjugated oligonucleotides: synthesis, properties, and activity as inhibitors of replication of human immunodeficiency virus in cell culture", Proc Natl Acad Sci USA 86:6553-6556.

Li et al., 1992, "Recommendations on predictive testing for germline p53 mutations among cancer-prone individuals", J. Natl. Cancer Inst. 84:1156-1160.

Lockhart et al., 1996, "Expression monitoring by hybridization to high-density oligonucleotide arrays", Nat Biotechnol 14:1675-1680.

Marks et al., 1992, "Molecular evolution of proteins on filamentous phage. Mimicking the strategy of the immune system", J Biol Chem 267:16007-16010.

Mascorro-Gallardo et al., 1996, "Construction of a CUP1 promoter-based vector to modulate gene expression in *Saccharomyces cerevisiae*", Gene 172:169-170.

Maskos and Southern, 1992, "Oligonucleotide hybridizations on glass supports: a novel linker for oligonucleotide synthesis and hybridization properties of oligonucleotides synthesised in situ", Nucleic Acids Res 20:1679-1684.

McBride and Caruthers, 1983, "An investigation of several deoxynucleoside phosphoramidites useful for synthesizing deoxyoligonucleotides", Tetrahedron Lett 24:245-248.

Microcompatibles Corporation. Scientific/Engineering Graphic Tools for the IBM PC and Compatibles. Science 1988 Guide to Biotechnology Products and Instruments. Feb. 12, 1988, Part. II. vol. 239, p. G77, advertisement at lower right corner.

Morgan and Roth, 1988, "Analysis of intracellular protein function by antibody injection", Immunol Today 9:84-88.

Morrison et al., 1984, "Chimeric human antibody molecules: mouse antigen-binding domains with human constant region domains", Proc Natl Acad Sci USA 81:6851-6855.

Mumberg et al., 1994, "Regulatable promoters of *Saccharomyces cerevisiae*: comparison of transcriptional activity and their use for heterologous expression", Nucleic Acids Res 22:5767-5768.

Neuberger et al., 1984, "Recombinant antibodies possessing novel effector functions", Nature 312:604-608.

Neumann HP et al., "Monogenetic hypertension and pheochromocytoma", Am J Kidney Dis. Sep. 1996;28(3):329-33.

Nguyen et al., 1995, "Differential gene expression in the murine thymus assayed by quantitative hybridization of arrayed cDNA clones", Genomics 29:207-216.

No D et al., "Ecdysone-inducible gene expression in mammalian cells and transgenic mice", Proc Natl Acad Sci U S A. Apr. 16, 1996;93(8):3346-51.

Nocka et al., 1990, "Molecular bases of dominant negative and loss of function mutations at the murine c-kit/white spotting locus: W37, Wv, W41 and W", EMBO J 9:1805-1813.

Paulus et al., 1996, "Self-contained, tetracycline-regulated retroviral vector system for gene delivery to mammalian cells", J Virol 70:62-67.

Pease et al., 1994, "Light-generated oligonucleotide arrays for rapid DNA sequence analysis", Proc Natl Acad Sci USA 91:5022-5026.

Perlmutter and Alberola-lla, 1996, "The use of dominant-negative mutations to elucidate signal transduction pathways in lymphocytes", Curr Opin Immunol 8:285-290.

Pettitt et al., 1996, "cdh-3, a gene encoding a member of the cadherin superfamily, functions in epithelial cell morphogenesis in Caenorhabditis elegans", Development 122:4149-4157.

Pietu et al., 1996, "Novel gene transcripts preferentially expressed in human muscles revealed by quantitative hybridization of a high density cDNA array," Genome Res. 6:492.

Prashar and Weissman, 1996, "Analysis of differential gene expression by display of 3' end restriction fragments of cDNAs", Proc Natl Acad Sci USA 93:659-663.

Ramirez-Solis et al., 1993, "Gene targeting in embryonic stem cells", Methods Enzymol 225:855-878.

Rozas et al., 1990, "Automatic processing of graphics for image databases in science", J.Chem. Inf. Comput. Sci. 20: 7-12.

Sagliocco et al., 1996, "Identification of proteins of the yeast protein map using genetically manipulated strains and peptide-mass fingerprinting", Yeast 12:1519-1533.

Sarin et al., 1988, "Inhibition of acquired immunodeficiency syndrome virus by oligodeoxynucleoside methylphosphonates", Proc Natl Acad Sci USA 85:7448-7451.

Sarver et al., 1990, "Ribozymes as potential anti-HIV-1 therapeutic agents", Science 247:1222-1225.

Schena et al., 1995, "Quantitative monitoring of gene expression patterns with a complementary DNA microarray", Science 270:467-470.

Shalon et al., 1996, "A DNA microarray system for analyzing complex DNA samples using two-color fluorescent probe hybridization", Genome Res 6:639-645.

Shevchenko et al., 1996, "Linking genome and proteome by mass spectrometry: large-scale identification of yeast proteins from two dimensional gels", Proc Natl Acad Sci USA 93:14440-14445.

Smith et al., 1995, Cancer Surveys, vol. 25: "Genetics and Cancer: A Second Look", Imperial Cancer Fund.

Spencer, 1996, "Creating conditional mutations in mammals", Trends Genet 12:181-187.

Spradling et al., 1995, "Gene disruptions using P transposable elements: an integral component of the *Drosophila* genome project", Proc Natl Acad Sci USA 92:10824-10830.

Stein et al., 1988, "Physicochemical properties of phosphorothioate oligodeoxynucleotides", Nucleic Acids Res 16:3209-3221.

Stern et al., 1996, "Evidence for a major gene for type II diabetes and linkage analyses with selected candidate genes in Mexican-Americans", Diabetes 45:563-568.

Straus and Weiss, 1992, "Genetic evidence for the involvement of the lck tyrosine kinase in signal transduction through the T cell antigen receptor", Cell 70:585-593.

Takeda et al., 1985, "Construction of chimaeric processed immunoglobulin genes containing mouse variable and human constant region sequences", Nature 314:452-454.

Thomas and Capecchi, 1987, "Site-directed mutagenesis by gene targeting in mouse embryo-derived stem cells", Cell 51:503-512.

Thorsness et al., 1989, "Positive and negative transcriptional control by heme of genes encoding 3-hydroxy-3-methylglutaryl coenzyme A reductase in *S.cerevisiae*", Mol. Cell. Biol. 9:5702-5712.

Tomlinson et al., 1997, "Molecular genetics of colon cancer", Cancer and Metastasis Reviews 16:67-79.

van der Krol et al., 1988, Modulation of eukaryotic gene expression by complementary RNA or DNA sequences. Biotechniques 6:958-976.

Velculescu, 1995, "Serial analysis of gene expression", Science 270:484-487.

Wagner, 1981, "Nucleotide sequence of the thymidine kinase gene of herpes simplex virus type 1", Proc Natl Acad Sci USA 78:1441-1445.

Weinstein et al., 1997, "An information intensive approach to the molecular pharmacology of cancer", Science, 275: 343-349.

Weisgraber and Mahley, 1996, "Human apolipoprotein E: the Alzheimer's disease connection", FASEB J. 10:1485-1494.

Yamamoto et al., 1980, "Identification of a functional promoter in the long terminal repeat of Rous sarcoma virus", Cell 22:787-797.

Zhao et al., 1995, "High-density cDNA filter analysis: a novel approach for large-scale, quantitative analysis of gene expression," Gene 156:207-213.

Zon, 1988, "Oligonucleotide analogues as potential chemotherapeutic agents", Pharm Res 5:539-549.

Ermolaeva et al., 1998, "Data management and analysis for gene expression arrays", Nature Genetics 20:19-23.

McClanahan et al., 1984, "Specific Transcripts Are Elevated in *Saccharomyces cerevisiae* in Response to DNA Damage", Molecular and Cellular Biology 4:2356-2363.

Michaels et al., 1997, "Cluster Analysis and Data Visualization of large Scale Gene Expression Data", Inst. for Computational Sciences and Informatics, pp. 42-53.

Hochhauser et al., 1996, "Effect of Cyclin D1 Overexpression on Drug Sensitivity in a Human Fibrocarcoma Cell Line," Journal of the National Cancer Institute, J. Nat. Cancer Inst. 88:1269-1275.

Kawamura et al., 1996, "A Multicopy Suppressor of nin1-1 of the yeast *Saccharomyces cerevisiae* is a counterpart of the *Drosophila melanogaster* diphenol oxidase A2 gene, Dox-A2," Mol Gen Genet 251:146-152.

Lashkari et al., 1997, "Yeast microarrays for genome wide parallel genetic and gene expression analysis", Nat. Acad. of Sciences USA 94:13057-13062.

Lemkin et al., 1995, "The Protein Database of human body fluids: II. Computer methods and data issues", Applied and Theoretical Electrophoresis, 5:55-72.

Kominami et al., 1997, "Yeast Counterparts of Subunits S5a and p58 (S3) of the Human 26S Proteasome Are Encoded by Two Multicopy Suppressors of *nin1-1*", Mol. Biol. Cell 8:171-187.

Merril et al., 1995, "The Protein Disease Database of human body fluids: I. Rationale for the development of this database", Applied and Theoretical Electrophoresis, 5:49-54.

Ruby et al., 1985, "Specific *Saccharomyces cerevisiae* Genes Are Expressed in Response to DNA-Damaging Agents", Mol. and Cell. Biol. 5:75-84.

Salas et al., 1998, "EpoDB: a database of genes expressed during vertebrate erythropoiesis", Nucleic Acids Res. 26:288-289.

Schena et al., 1996, "Parallel human genome analysis: Microarray-based expression monitoring of 1000 genes", Proc. Natl. Acad. Sci. USA 93:10614-10619.

Shoemaker et al., 1996, "Quantitative phenotypic analysis of yeast deletion mutants using a highly parallel molecular bar-coding strategy" Nature Genet. 14: 450-456.

* cited by examiner

COMPUTER SYSTEMS AND COMPUTER PROGRAMS FOR DETERMINING PROTEIN ACTIVITY LEVELS USING GENE EXPRESSION PROFILES

This application is a division of U.S. patent application Ser. No. 09/303,082, filed Apr. 30, 1999, now U.S. Pat. No. 6,324,479, which claims the benefit of U.S. Provisional Patent Application No. 60/084,742, filed on May 8, 1998, and of U.S. Provisional Patent Application No. 60/090,046, filed on Jun. 19, 1998, all of which are incorporated herein by reference in their entireties.

1. FIELD OF THE INVENTION

The field of this invention relates to methods for determining the partial inactivation of proteins in cells, and for analyzing situations in which protein activity levels are partially disrupted. The invention also relates to the application of these methods to identify individuals who have genetic polymorphisms and mutations that disrupt the function of important genes. Further, the invention relates to the application of these methods to identify the activity of drugs in vivo.

2. BACKGROUND

Within the past decade, several technologies have made it possible to monitor the expression level of a large number of transcripts within a cell at any one time (see, e.g., Schena et al., 1995, Quantitative monitoring of gene expression patterns with a complementary DNA micro-array, Science 270:467–470; Lockhort et al., 1996, Expression monitoring by hybridization to high-density oligonucleotide arrays, Nature Biotechnology 14:1675–1680; Blanchard et al., 1996, Sequence to array: Probing the genome's secrets, Nature Biotechnology 14, 1649; 1996, U.S. Pat. No. 5,569, 588, issued Oct. 29, 1996 to Ashby et al. entitled "Methods for NY2-1221902.1 Drug Screening"). In organisms for which the complete genome is known, it is possible to analyze the transcripts of all genes within the cell. With other organisms, such as human, for which there is an increasing knowledge of the genome, it is possible to simultaneously monitor large numbers of the genes within the cell.

Early applications of this technology have involved identification of genes which are up regulated or down regulated in various diseased states. Additional uses for transcript arrays have included the analyses of members of signaling pathways, and the identification of targets for various drugs. However, because proteins are regulated by many different processes that include, not only transcription, but also translational controls and post-translational controls, it has not previously been recognized that transcript arrays might be beneficial in analyzing differential activity of proteins.

However, the ability to monitor minor differences in protein activity levels would be of great human and commercial value. For example, most genetic mutations that produce a diseased state do so by disrupting the activity level of the corresponding gene product. Thus, the ability to determine disruption or partial disruption of activity of a particular gene product, i.e., a particular protein, in cells provides a useful means for identifying those individuals having genetic mutations and/or polymorphisms that disrupt the function of important proteins. In particular, there are numerous cancer susceptibility genes, numerous genes that determine metabolism of drugs, and genes that determine the presence of numerous disease states which, if altered in one of the two alleles, would provide an increased risk for a large set of health related problems. Examples of such genes, which are referred to herein as "susceptibility genes", include, but are not limited to, BRCA1 and BRCA2, which are associated with greatly increased susceptibility to breast and ovarian cancer (Cannon-Albright and Skolnick, 1996, Seminars in Oncology 23:1–5), APC which is associated with an increased susceptibility to colon cancer (Tomlinson et al., 1997, Cancer and Metastasis Reviews 16:67–79; and Cunningham and Dunlop, 1996, British Journal of Surgery 83:321–329), p16/CDKN2A which is associated with an increased susceptibility to cutaneous melanoma (Haluska and Hodi, 1998, Journal of Clinical Oncology 16:670–682), RET and VHL which are associated with an increased susceptibility to pheochromocytoma and hypertension (Hartmut et al., 1996, American Journal of Kidney Diseases 28:329–333), AT1R which is associated with diabetic nephropathy (Chowdhury et al., 1997, Diabet. Med. 14:837–840), IRS1 which is associated with type II diabetes (Stern et al., 1996, Diabetes 45:563–568), apoE which is associated with Alzheimer's disease (Weisgraber and Mahley, 1996, FASEB J. 10:1485–1494), and p53 which is associated with several types of human cancers (see, e.g., Friend, 1994, Science 265:334–335; Frebourg and Friend, 1992, J. Clin. Invest. 90:1637–1641; and Li et al., 1992, J. Natl. Cancer Inst. 84:1156–1160). For a review of polymorphisms that affect drug metabolism in humans see, e.g., Smith et al., 1995, Cancer Surveys, vol. 25: "Genetics and Cancer: A Second Look", Imperial Cancer Research Fund.

In particular, there is a need for methods for identifying individuals having heterozygous mutations, i.e., mutations in which one of the two alleles of a gene is altered. Direct detection of heterozygous mutations is problematic with PCR since the wild type copy of the gene is also present. Further, the exact sequence of the mutated gene copy will not, in general, be known. Additionally, the genotype of a mutation is not as direct an indication of protein function as are the effects of the protein itself. Consequently, the monitoring of protein function is often a superior indicator of a disease state or disease susceptibility compared to genotyping, since the protein activity level is more directly related to organism function (see, e.g., Brown and Hartwell, 1998, Nature Genetics 18:91-93). Direct monitoring of protein function in heterozygote carriers is ofter difficult, however, because assays are complex and monitoring of 50% or less decrease in overall activity can be difficult biochemically.

Methods for analyzing differential function of proteins would also be useful to monitor the activity of drugs in cells, in vivo. Currently, it would be a great benefit if one could assay for diminished activities that drugs have over time in a way that is not dependent upon independently characterizing individual metabolic breakdown products.

Thus, there is a need for methods of monitoring the activity levels of proteins in cells. In particular, there is a need for methods for monitoring protein activity in cells which thereby make it possible to identify individuals who have genetic mutations and/or polymorphisms that disrupt the activity of important proteins, and are associated with diseased states or with an increased susceptibility to certain diseased state. Further, there is a need for methods of monitoring protein activity in cells which allow for identifying the activity of drugs in vivo.

Discussion or citation of a reference herein shall not be construed as an admission that such reference is prior art to the present invention.

3. SUMMARY OF THE INVENTION

The present invention provides methods for determining the level of activity, for example due to partial inactivation, of cellular constituents, such as proteins, in cells. The invention also provides methods for analyzing situations in which the activity of a particular cellular constituent, specifically the activity of a particular protein, is changed (e.g., is disrupted, partially disrupted, or increased). The methods of the invention involve comparing a "diagnostic profile", obtained by measuring RNA or protein abundances or activities in a cell in which the activity of a specific "target" protein is suspected of being partially changed, with "response curves", which are obtained by measuring RNA or protein abundances or activities in cells in response to controlled, known perturbations of the target protein. The known protein perturbations are controlled to be of varying strengths over a substantial part of the range from complete disruption to no disruption of protein activity, or to a level of increased protein activity.

The methods of the invention can also be used to determine the activity levels of a plurality of proteins in a cell by comparing a diagnostic profile with a combination of response curves for the individual proteins whose activities are to be determined.

The present invention also provides methods for identifying individuals who have genetic polymorphisms or mutations that disrupt the function of important genes and their corresponding gene products, i.e., the cellular constituents encoded by such genes. The methods involve comparing a diagnostic profile, obtained by measuring gene or protein abundances in cells from individuals suspected of having a genetic mutation or polymorphism that directly disrupts or partially disrupts the activity of a target protein, with response curves which are obtained by measuring RNA or protein abundances or activities in cells in response to controlled, known perturbations of the target protein.

The present invention further provides methods for determining the activity level of drugs in vivo. Specifically, the invention provides methods for identifying the activity of drugs which inhibit the activity of specific cellular constituents, particularly specific proteins. The methods involve comparing a diagnostic profile, obtained by measuring gene or protein abundances in a cell which has been treated over time with a drug or drugs that directly inhibit a target protein, with response curves which are obtained by measuring gene or protein abundances in cells in response to controlled, known perturbations of the target protein.

The methods of this invention are based on the discovery that a disruption of the activity of a given protein within a cell results in characteristic changes in the transcription and activity of other genes, and that such changes can be used to define a "signature" of particular transcript alterations which are related to the disruption of the function of the protein. This is true even if there is only partial disruption of the activity level of the given protein, e.g., a disruption of the activity level by less than 50%.

In more detail, the present invention provides methods for determining or estimating the partial disruption of protein activity levels in a cell by: (i) obtaining a diagnostic profile by measuring abundances of cellular constituents in a cell in which the activity of a specific protein is suspected of being partially disrupted; (ii) obtaining response curves by, first, obtaining response profiles by measuring abundances of cellular constituents that occur in a cell in response to perturbations of said protein, and second, interpolating the thus obtained response profiles; and (iii) determining the protein activity level at which the response profile extracted from the response curve best fits the measured diagnostic profile, according to some objective measure. In various embodiments, the profile of the cell can be determined by measuring gene expression, protein abundances, protein activities, or a combination of such measurements. In various embodiments, the perturbation to protein activity can be made by use of titratable expression systems, use of transfection systems, modification to abundances of protein RNAs, modifications of abundances of protein, or modifications to activity of the protein.

In a first embodiment, the invention provides a method of determining levels of activity of one or more proteins in a cell type, comprising determining a level of perturbation to each said protein at which similarity is greatest between a diagnostic profile and a combination of perturbation response profiles extracted from perturbation response curves for each said protein for said determined level of perturbation, wherein said diagnostic profile is provided by a method comprising measuring a plurality of cellular constituents in a cell of said cell type, wherein said perturbation response curves for each said protein are the products of a method comprising (i) providing perturbation response profiles of said protein for said cell type, wherein said perturbation response profiles are obtained by measuring a plurality of cellular constituents in a cell of said cell type at a plurality of discrete levels of perturbation to said protein, and (ii) interpolating said perturbation response profiles so that a perturbation response profile may be extracted for any level of perturbation to said protein, wherein said interpolated response profiles comprise said perturbation response curves, wherein said levels of perturbation to each said protein represent the level of activity of each said protein in said cell type.

In a preferred aspect of the first embodiment, protein activity expression levels are quantitated for each level of perturbation to said protein, and said quantitated protein activity levels are normalized to the wild type protein activity level so that the levels of perturbation may be expressed as functions of %-protein activity. In another preferred aspect of the first embodiment, the invention further provides that said determining step further comprises determining the actual minimized value of said objective function.

In another preferred aspect of the first embodiment, the determined level of perturbation in step (c) is the level of perturbation which minimizes an objective function of the difference between the diagnostic profile and the perturbation response profile extracted from the perturbation response curves.

In a second embodiment, the present invention provides a method of identifying cells of a cell type that have genetic mutations or polymorphisms that disrupt activity of their corresponding gene products. The method of this second embodiment comprises determining a level of perturbation to each said gene product at which similarity is greatest between a diagnostic profile and perturbation response profiles extracted from perturbation response curves for each said protein for said determined level of perturbation, said diagnostic profile having been obtained by a method comprising measuring a plurality of cellular constituents in a cell of said cell type, wherein said perturbation response curves for each said gene product are the product of a method comprising (i) providing perturbation response profiles of said gene product for said cell type, wherein said perturbation response profiles are obtained by measuring a plurality of cellular constituents in a cell of said cell type at a plurality of discrete levels of perturbation to said gene product, and (ii) interpolating said perturbation response profiles so that a perturbation response profile may be extracted for any level of perturbation to said gene product, wherein said interpolated response profiles comprise said perturbation response curves, wherein said levels of perturbation to each said gene product represent the level of activity of each said protein in said cell type.

In one aspect of the second embodiment, the method is used to identify individuals having a genetic mutation that disrupts protein activity of a corresponding gene product using cells derived from said individual to assay said protein activity level. In another aspect of the second embodiment, the method is used to identify cells having a heterozygous mutation that disables one of the two alleles of a gene.

In a third embodiment, the present invention provides a method for measuring the activity of drugs in vivo, comprising determining, according to the method of the first embodiment, the activity level of one or more proteins in a cell treated over time with one or more drugs that interact with said proteins, wherein the extent to which said protein activity levels are disrupted is a measure of the activity of said drugs.

The invention also provides, in a fourth embodiment, a method for determining the dose of one more drugs to achieve a desired clinical effect in a patient. The method comprises determining the dose of the one or more drugs at which similarity is greatest between a diagnostic profile and a perturbation response profile associated with the desired clinical effect. In such an embodiment, the perturbation response profile is preferably extracted from perturbation response curves (i.e., from a plurality of interpolated perturbation response profiles) which are calibrated in terms of clinical effects of the one or more drugs. In an alternative of the fourth embodiment, the methods of the invention are used to determine a drug therapy to achieve a desired clinical effect in a patient. The method of this alternative comprises determining the drug therapy so that similarity is greatest between a diagnostic profile and a perturbation response profile associated with the desired clinical effect.

In a fifth embodiment, this invention provides a computer system for analyzing the activity level of one or more proteins in a cell type. The computer system of the invention comprises a processor and memory coupled to said processor, said memory encoding one or more programs, said one or more programs causing said processor to perform a method comprising the steps of (a) receiving a diagnostic profile of a cell of said cell type, said diagnostic profile having been obtained by a method comprising measuring a plurality of cellular constituents in a cell of said cell type; (b) receiving perturbation response curves of said activity levels of each said proteins for said cell type wherein said perturbation response curves for each said protein are the products of a method comprising (i) receiving perturbation response profiles of said protein for said cell type, wherein said perturbation response profiles are obtained by measuring a plurality of cellular constituents in a cell of said cell type at a plurality of discrete levels of perturbation to said protein, and (ii) interpolating said perturbation response profiles so that a perturbation response profile may be extracted for any level of perturbation to said protein, wherein said interpolated response profiles comprise said perturbation response curves; (c) determining the value of an objective function of the difference between said diagnostic profile and a combination of the perturbation response profile extracted from said perturbation response curves for level of perturbation to each said protein; and (d) minimizing said determined value of said objective function by varying the level of perturbation to each said protein to obtain a combination of perturbation response profiles that minimize said determined value of said objective function, wherein said level of perturbation to each said proteins represent the level of activity of each said protein in said cell type.

In a particular aspect of the fifth embodiment, said programs cause said processor to perform said step (b)(ii) of interpolating said perturbation response profiles.

4. BRIEF DESCRIPTION OF THE DRAWINGS

FIG. 1 illustrates exemplary responses of expression response to the deletion of one of the two (diploid) copies of the SUN2 gene in the yeast *Saccharomyces cerevisiae*; $\log^{10}$ of the ratio of mRNA expression level in the deletion mutant to the expression level in the wild type strain is plotted on the vertical axis, vs. hybridization intensity, which is roughly proportional to molecular abundance of transcripts, on the horizontal axis; genes whose mRNA expression consistently increased or decreased in five repeated experiments are labeled, and flagged with error bars that indicate the standard deviation of the five repeated measurements.

FIG. 2 illustrates response curves of the 30 yeast genes, out of approximately 6000 measured yeast genes, that had the largest expression ratio changes to methotrexate drug exposure; methotrexate exposure levels were 3, 6, 25, 50, 100, and 200 μM; the 100 μM titration resulted in a 50% growth defect; responses have been set to zero at the arbitrary abscissa of −0.5.

5. DETAILED DESCRIPTION

Figure 1:
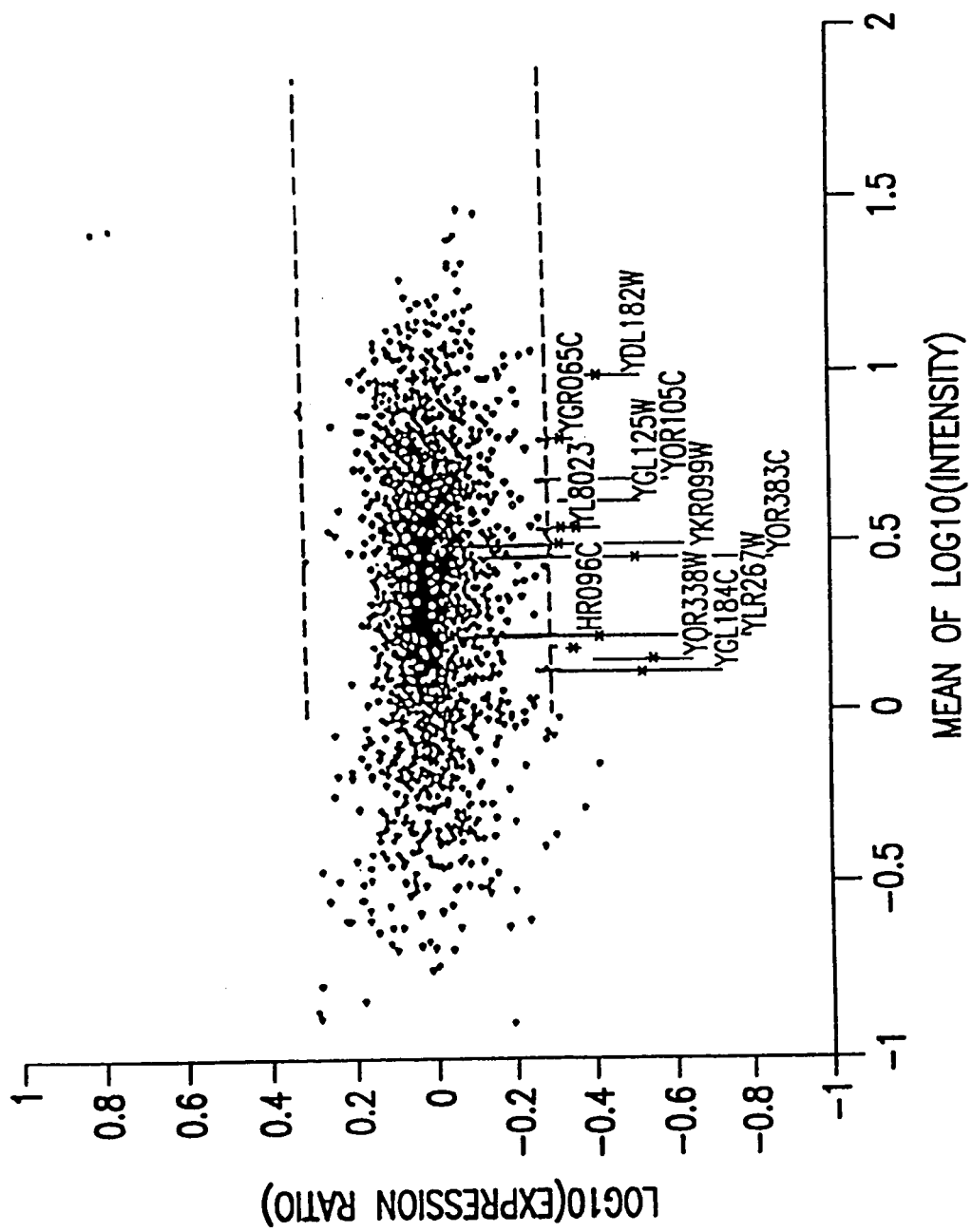

This section presents a detailed description of the present invention and its applications. This description is by way of several exemplary illustrations, in increasing detail and specificity, of the general methods of this invention. These examples are non-limiting, and related variants that will be apparent to one of skill in the art are intended to be encompassed by the appended claims. Following these examples are descriptions of embodiments of the data gathering steps that accompany the general methods.

5.1. Introduction

The present invention includes methods for determining the partial inactivation of proteins within a biological system (e.g., a cell, particularly a eukaryotic cell, or an organism, including a human). These methods involve comparing measurements of the biological state of a cell for which protein activity is to be determined with measurements of changes in the biological state of a cell in response to known, controlled perturbations of the activity of a protein.

This section first presents certain concepts, including protein activity level and biological state. Next, a schematic and non-limiting overview of the methods of the invention is presented. The following sections present the methods of the invention in greater detail.

Although for simplicity this disclosure often makes references to single cell (e.g., "RNA is isolated from a cell perturbed at a single gene"), it will be understood by those of skill in the art that more often any particular step of the invention will be carried out using a plurality of genetically similar cells, e.g., from a cultured cell line. Such similar cell are called herein a "cell type". Such cells are derived either from naturally single celled organisms, or derived from multi-cellular higher organisms (e.g., human cell lines).

In particular, Section 5.1 describes certain preliminary concepts of the present invention. Section 5.2 generally describes the methods of the invention. Section 5.3 describes a preferred analytic embodiment of the methods of the invention. Section 5.4 describes methods of perturbing biological pathways. Section 5.5 describes methods of measuring cellular constituents. Finally, Section 5.6 describes certain applications of the present invention first, to identifying individuals having genetic mutations and/or polymorphisms which disrupt the function of important genes, and, second, to identify the activity of drugs in vivo.

Protein Activity Level

According to the present invention, protein activity refers to protein mediated effects on the state of a biological system, whether by known or unknown mechanisms. The biological effect of a protein may be a consequence of, inter alia, protein mediated regulation of the transcription or degradation of one or more species of RNA, protein mediated regulation of translation or post-translational processing of one or more polypeptides, protein mediated catalysis of biochemical reactions, protein mediated transport or storage of biologically active molecules such as nutrients, and so forth.

In addition to proteins, this invention is equally applicable to other cellular constituents i.e., cellular constituents that affect the state of a biological system. Such components may include, for example, ribozyme and transfer RNAs. As used herein, the term "cellular constituents" is not intended to refer to known subcellular organelles, such as mitochondria, lysosomes, etc.

The activity level of a protein or other cellular constituent is therefore a measure of the extent to which the protein or other cellular component affects a biological system. Activity levels of a protein or other cellular constituent are also referred to herein as "biological activity levels". Biological activity levels, particularly protein activity levels, are affected by, inter alia, factors which affect the function of proteins, including drugs which interact with proteins and genetic mutations or polymorphisms which encode mutant forms of proteins, as well as factors which affect the amount of protein in a biological system, such as drugs which affect the transcription of genes that encode proteins, drugs which affect the translation of mRNAs that encode proteins, or drugs which affect the degradation rate of proteins, as well a genetic mutations or polymorphisms that affect the transcription, translation, or degradation of the gene product, i.e., protein. Such mutations include heterozygous mutations wherein one allele of a diploid gene is disabled, i.e., encodes a mutant protein with altered or no activity. Although much of the description of the present invention is directed to determining protein activity levels, it will be apparent to those of skill in the art that the methods of this invention are equally applicable to determining activity levels of other cellular constituents.

Biological State

The activity level of a protein (or other biologically active component) is measured in the instant invention by observing the biological state of a cell. The biological state of a cell, as used herein, is taken to mean the state of a collection of cellular constituents, which are sufficient to characterize the cell for an intended purpose, such as for characterizing the effects of a drug. The measurements and/or observations made on the state of these constituents can be of their abundances (i.e., amounts or concentrations in a cell), or their activities, or their states of modification (e.g., phosphorylation), or other measurement relevant to the characterization of drug action. In various embodiments, this invention includes making such measurements and/or observations on different collections of cellular constituents. These different collections of cellular constituents are also called herein aspects of the biological state of the cell.

One aspect of the biological state of a cell usefully measured in the present invention is its transcriptional state. The transcriptional state of a cell includes the identities and abundances of the constituent RNA species, especially mRNAs, in the cell under a given set of conditions. Preferably, a substantial fraction of all constituent RNA species in the cell are measured, but at least, a sufficient fraction is measured to characterize the action of a drug of interest. The transcriptional state is the currently preferred aspect of the biological state measured in this invention. It can be conveniently determined by, e.g., measuring cDNA abundances by any of several existing gene expression technologies.

Another aspect of the biological state of a cell usefully measured in the present invention is its translational state. The translational state of a cell includes the identities and abundances of the constituent protein species in the cell under a given set of conditions. Preferably, a substantial fraction of all constituent protein species in the cell are measured, but at least, a sufficient fraction is measured to characterize the action of a drug of interest. As is known to those of skill in the art, the transcriptional state is often representative of the translational state.

Other aspects of the biological state of a cell are also of use in this invention. For example, the activity state of a cell, as that term is used herein, includes the activities of the constituent protein species (and also optionally catalytically active nucleic acid species) in the cell under a given set of conditions. As is known to those of skill in the art, the translational state is often representative of the activity state.

This invention is also adaptable, where relevant, to "mixed" aspects of the biological state of a cell in which measurements of different aspects of the biological state of a cell are combined. For example, in one mixed aspect, the abundances of certain RNA species and of certain protein species, are combined with measurements of the activities of certain other protein species. Further, it will be appreciated from the following that this invention is also adaptable to other aspects of the biological state of the cell that are measurable.

Perturbations in activity levels will affect many constituents of whatever aspects of the biological state of a cell are being measured and/or observed in a particular embodiment of the present invention. In particular, as a result of regulatory, homeostatic, and compensatory networks and systems known to be present in cells, even the direct disruption of only a single constituent in a cell, without directly affecting any other constituent, will have complicated and often unpredictable indirect effects.

The inhibition of a single, hypothetical protein, protein P is considered herein as an example. Although the activity of only protein P is directly disrupted, additional cellular constituents that are inhibited or stimulated by protein P, or which are elevated or diminished to compensate for the loss of protein P activity will also be affected. Still other cellular constituents will be affected by changes in the levels or activity of the second tier constituents, and so on. These changes in other cellular constituents can be used to define a "signature" of alterations of particular cellular constituents which are related to the disruption of a given cellular constituent.

Measurement of the transcriptional state of a cell is preferred in this invention, not only because it is relatively easy to measure but also because, even though a protein of interest may not directly modulate transcription, the disruption of protein activity in a cell almost always results in a measurable change, through direct or indirect effects, in the transcriptional state. A reason that disruption in a protein's activity level changes the transcriptional state of a cell is because the previously mentioned feedback systems, or networks, which react in a compensatory manner to infections, genetic modifications, environmental changes, drug administration, and so forth do so primarily by altering patterns of gene expression or transcription. As a result of internal compensations, many perturbations to a biological system, although having only a muted effect on the external behavior of the system, can nevertheless profoundly influence the internal response of individual elements, e.g., gene expression, in the cell.

5.2. Determining Protein Activity from Expression Profiles

This section presents, first, and overview of the methods of this invention, and second, an extended illustrative example of the principal of these methods.

Overview of the Methods of this Invention

The methods of this invention determine the in vivo activity level of a protein in a cell, and, more specifically, detect changes in the in vivo activity levels of a protein caused by, e.g., mutations of one or both alleles of a gene, or by inhibition of a protein by a drug. As used herein, an "expression profile" comprises measurement of a plurality of cellular constituents that indicate aspects of the biological state of a cell. Such measurements may include, e.g., RNA or protein abundances or activity levels.

Aspects of the biological state of a cell, for example, the transcriptional state, the translational state, or the activity state, are measured as described in Section 5.5. The collection of these measurements, optionally graphically represented, is called herein the "diagnostic profile". Aspects of the biological state of a cell which are similar to those measured in the diagnostic profile, e.g., the transcriptional state, are measured in response to a plurality of graded protein perturbation strengths, i.e., for a plurality of "perturbation levels". The collection of these measurements, optionally graphically represented, is called herein the "response profile" or "perturbation response profile". The response profiles are interpolated to predict response profiles for all levels of protein activity within the range of protein activity measured. The collection of interpolated response profiles, optionally graphically represented, is called herein the "response curve".

The response profiles are preferably measured in experiments in which the activity or abundance of the protein or its gene is changed. The response curves are also preferably expressed as functions of %-protein activity, or, less preferably, as functions of the perturbation parameter used to manipulate the protein.

Cellular constituents in the diagnostic profile are compared to cellular constituents varying in the response curves in order to find a perturbation strength, i.e., a protein activity level, for which the perturbation profile matches all or substantially all of the diagnostic profile. Substantially all of a diagnostic profile is matched by a response profile when most of the cellular constituents which vary in the response curves are found to have substantially the same value in the two profiles. Preferably, at least 75% of the cellular constituents varying in the response curves can be matched, more preferably at least 90% can be so matched. Cellular constituents have substantially the same value in the two profiles when both sets of data are likely to be the same in view of experimental error.

In a preferred embodiment, comparison of a diagnostic profile with response curves is performed by a method in which an objective measure of difference between a measured diagnostic profile and a perturbation response profile extracted from the perturbation response curves for some perturbation level, i.e., for some protein activity level. The objective measure can be minimized by adjusting the protein activity level in the perturbation curves and extracting the perturbation response profile for corresponding to adjusted protein activity level. Minimization of the objective measure can be performed by standard techniques of numerical analysis. See, e.g., Press et al., 1996, *Numerical Recipes in C*, 2nd Ed. Cambridge Univ. Press, Ch. 10.; Branch et al., 1996, *Matlab Optimization Toolbox User's Guide*, Mathworks (Natick, Mass.).

Illustration of the Methods of the Present Invention

Figure 2:
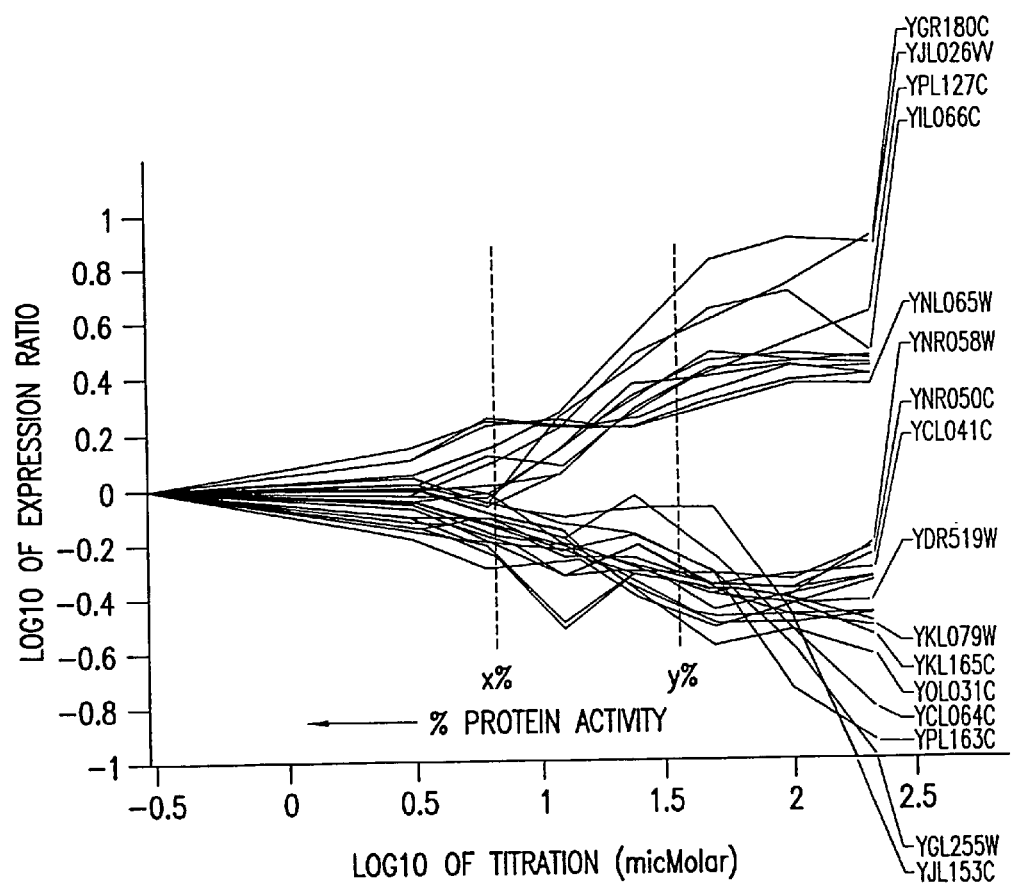

The following paragraphs which generally illustrate several of the methods of the present invention with respect to FIG. 1 and FIG. 2, are presented by way of example but not limitation. Within eukaryotic cells, there are hundreds to thousands of signaling pathways that are interconnected. For this reason, perturbations in the function of proteins within a cell have numerous effects on other proteins and the transcription of other genes that are connected by primary, secondary, and sometimes tertiary pathways. This extensive interconnection between the function of various proteins means that the alteration of any one protein is likely to result compensatory changes in a wide number of other proteins. In particular, even the partial disruption of a single protein with a cell, e.g., by addition of a drug or by changing the level of the protein by modulating the gene copy number, results in characteristic changes in the transcription of enough other genes that these changes in transcripts can be used to define a "signature" of particular transcript alterations which are related to the disruption of function, i.e., activity, of a given protein.

FIG. 1 illustrates an example of a diagnostic profile measured in a deletion mutant of the yeast *Saccharomyces cerevisiae* wherein one of the two (i.e., diploid) copies of the SUN2 gene is disabled. The figure illustrates mRNA expression levels of the approximately 6000 genes in the genome of this yeast. Specifically, the $\log_{10}$ of the ratio of mRNA expression level in the deletion mutant to the expression level in the wild type strain is plotted on the vertical axis, vs. hybridization intensity, which is roughly proportional to molecular abundance, on the horizontal axis. These gene expression level measurements were made with gene transcript arrays, as described in Section 5.4. Genes which were consistently up- or down-regulated in repeated experiments are labeled and flagged with error bars. These error bars indicate the standard deviation in the five repeated measurements for each gene transcript obtained from five microarrays.

Although the SUN2 gene product is not known to be a transcription factor, there are fifteen genes up- or down-regulated by more than a factor of two in response to this heterozygous deletion. Table I, below, shows the $\log_{10}$ of the factor by which the mRNA expression changed for those genes whose expression changed by more than a factor of two. Many of these changes are significantly more than the standard deviation. Measurement of the transcription level of the SUN2 gene itself shows its mRNA expression level is reduced less than a factor of two by the reduction in gene copy number from two to one. Thus, the protein activity level has almost certainly been reduced by less than a factor of two. Nevertheless, there is a distinct response in the expression profile of other genes.

TABLE I

| ORF | $\log_{10}$ (R/G) | +/− StdDev | R/G |
| --- | --- | --- | --- |
| YGR065C | −0.31 | 0.03 | 0.48 |
| YKR099W | −0.32 | 0.27 | 0.48 |
| YLR023C | −0.33 | 0.05 | 0.47 |
| YHR096C | −0.35 | 0.05 | 0.47 |
| YMR097C | −0.36 | 0.06 | 0.44 |
| YJR088W | −0.37 | 0.05 | 0.42 |
| YMR011W | −0.4 | 0.12 | 0.4 |
| YKR069W | −0.4 | 0.02 | 0.4 |
| YGL125W | −0.4 | 0.08 | 0.4 |
| YBR105C | −0.41 | 0.12 | 0.39 |
| YDL182W | −0.41 | 0.09 | 0.39 |
| YLR267W | −0.42 | 0.34 | 0.38 |
| YOR383C | −0.47 | 0.34 | 0.34 |
| YGL184C | −0.48 | 0.21 | 0.33 |
| YOR338W | −0.51 | 0.1 | 0.31 |

By measuring gene expression at different percent inhibitions of the protein target, it is possible to construct response curves that show the effects of inhibition of a given protein long before there is a 50% inhibition of protein function. The resultant up regulation and down regulation of genes within a cell when the activity level of a protein is disrupted or partially disrupted represent compensatory changes that the cell undertakes in order to maintain homeostasis. As these compensatory changes in transcription occur before the cell exhibits any discernable physiological change, these expression profiles are very sensitive indications of the inhibition of protein function. This sensitivity has a significant value when it comes to diagnosing the presence of inactivating mutations in one of the two alleles, and also in monitoring the inhibition of proteins that are the targets of drugs.

FIG. 2 illustrates an example of perturbation response profiles measured at discrete protein activity levels of dihydrofolate reductase. Specifically, the figure illustrates mRNA expression levels of 30 genes of the yeast *Saccharomyces cerevisiae* that, of the 6000 genes in the genome of this yeast, had the largest expression changes in response to six different titrations of the drug methotrexate, which is known to act primarily by disrupting the activity of dihydrofolate reductase. These gene expression level measurements were made with gene transcript arrays, as described in Section 5.5. The perturbation response profiles in FIG. 2 can be interpolated according to the methods disclosed in Section 5.4, below, to provide perturbation response profiles for any activity level of dihydrofolate reductase, i.e., perturbation response curves.

The reduction in protein activity with increasing drug concentration is indicated qualitatively on FIG. 2, but the actual %-protein activity for any drug concentration is unknown without direct quantitation of the protein. If the relation of the concentration of drug to %-protein activity can be established, then any expression profile, i.e., any set of expression changes in response to a drug treatment at a particular concentration, can be interpreted as a certain %-protein activity by finding the horizontal location on the response curves that best matches the profile in question. For example, an observed set of transcriptional changes may match the pattern defined by the intersection of the vertical line marked 'x %' with the response curves in FIG. 2, while another set may match the pattern defined by the 'y %' line. The set of response curves in FIG. 2 thereby become a calibrated 'look-up' for %-protein activity. Less preferably, the protein activity level can be expressed in terms of concentration of drug wherein it will be understood, in the present example, that higher concentrations of methotrexate correspond to lower dihydrofolate reductase.

Perturbation response profiles such as those shown in FIG. 2 can be generated and measured by the perturbation methods described in Section 5.3, below. Such perturbation methods include, but are by no means limited to, controllable gene promoters adjusting the transcription rate, transfections of varying gene dosage, and drugs of known specific action against the protein in question. In particular, by employing technologies for gene expression analysis in concert with the genome sequence of the yeast *S. cerevisiae*, such response curves can be experimentally generated for nearly all of the genes in that organism. Although, much of the description of this invention is directed to measurement and modeling of gene expression data, this invention is equally applicable to measurements of other aspects of the biological state of a cell, such a protein abundances or activities.

Methods for direct measurement of protein activity are well known to those of skill in the art. Such methods include, e.g., methods which depend on having an antibody ligand for the protein, such as Western blotting (see, e.g., Burnette, 1981, A. Anal. Biochem. 112:195–203). Such methods also include enzymatic activity assays, which are available for most well-studied protein drug targets, including, but not limited to, HMG CoA reductase (Thorsness et al., 1989, Mol. Cell. Biol. 9:5702–5712), and calcineurin (Cyert et al., 1992, Mol. Cell. Biol. 12:3460–3469). An example of turning off a specific gene function by turning off the controllable promoter, and correlating this with protein depletion via Western blotting is given in Deshaies et al., 1988, Nature 332:800–805.

By simultaneously quantitating protein activity and gene expression in the biological samples obtained for each value of the perturbation parameter, and normalizing them to wild type protein activity level, such response curves may be expressed as function of %-protein activity rather than as functions of the perturbation parameter used to manipulate the protein. Alternatively, it is possible that direct quantitation of the protein activity may not be necessary in certain embodiments. For example, experience with the controllable promoter system of choice may allow estimating %-protein activity based on the concentration of the control compound without verifying the actual protein activity level for each protein under study.

As suggested by the discrete points in FIG. 2, perturbations to the protein are actually applied at a limited set of discrete values, and the perturbation curves are actually expression ratio values interpolated these discrete perturbation control parameter values, i.e., the curves are actually comprised of interpolated, discrete perturbation response profiles. It is expected that in order to allow robust interpretation to any protein activity level in the perturbation response curves, expression profiles and protein activity sampling will need to be roughly three samples per decade of perturbation parameter. For example, preferably, seven or more perturbation parameter values will be required to cover two decades in parameter values. More preferably, the discrete perturbation values are chosen and positioned so that the steepest regions of the pathway response curves are adequately sampled, with at least 5, and more preferably 10 or more, perturbation control parameter values positioned in the regions of the response curves where the responses vary from the unexposed level to the saturating level.

In other embodiments, it is expected that the number of perturbation control parameter values will be limited. For example, the range of perturbation procedure may be limited in human systems since there is little freedom for experimentation. Passive procedures for obtaining the required gene expression response curves and protein activity data are therefore employed in such systems. Passive procedures for obtaining gene expression response curves and protein activity data include, e.g., taking tissue or blood samples from individuals already undergoing regimens of drug treatment at varying dosages, and also using individuals with known heterozygous mutations for at least one intermediate protein activity data point.

The perturbation response curves in FIG. 2 illustrate the generally expected shape of such curves. This expected shape includes a below threshold region of low perturbation control parameter over which there is effectively no response of the cellular constituents to the perturbation. After this below threshold region, the drug or perturbation begins to be efficacious, and the values of characteristics of the cellular constituents are perturbed. The curve of perturbed values is expected to usually have a monotonic increase or decrease toward an asymptotic level at saturation, beyond which no further change is observed. The response curves terminate in this saturation region.

In fact, more complicated, non-monotonic response curve shapes are possible and expected in some situations. For example, in the case where the perturbation has toxic effects, as toxicity sets in rising abundances of cellular constituents may start to fall, and falling abundances may start to fall even faster. Also, nonlinear and feed back mechanisms known to be present in the biological system may result in non-monotonic, multi-phasic responses. Such a response might first increase and then decrease with increasing perturbation amplitude or drug exposure. For example, a perturbation may act on certain cellular constituents through two pathways with different thresholds and with opposite effects to generate increasing and then decreasing (or vice versa) responses. Although the methods of this invention are illustrated and primarily described with respect to monotonic response curves, such as those illustrated in FIG. 2, as will be apparent to one of skill in the art from subsequent description, these methods are equally applicable to non-monotonic response curves.

5.3. Analytic Embodiments

The analytic embodiments of the methods of the present invention include embodiments for evaluating the difference between a diagnostic profile and a response profile at a particular protein activity level by some objective function. A flow chart for a preferred embodiment of the methods of this invention is set out in FIG. 3. This embodiment determines representative perturbation response profile data 301 for a particular protein at a plurality of discrete, controlled, known protein activity levels. Diagnostic profile data 302 is then compared with the response profile data at step 303 from which a protein activity level is determined. In other embodiments of this invention, certain steps illustrated in FIG. 3 may be omitted or performed in orders other than as illustrated. For example, in certain embodiments step 301 of obtaining perturbation response profile data will already be derived for a certain protein, or for several, preferably related, proteins, and need not be performed separately for each protein activity analysis.

5.3.1. Expression Profile Representation

The analysis of protein activity levels preferably begins at step 301 by measuring perturbation response profiles. In many cases perturbation response profiles will have already been measured for perturbations of the selected protein. In other cases, this response data must be measured prior to the succeeding steps of this invention. As described above, perturbation profiles for a protein include measurements of relative changes in relevant characteristics of the cellular constituents for a plurality of known, controlled levels of a perturbation to the protein activity. More specifically, the activity of the protein of interest is perturbed in a graded manner, and the resulting ratios (or logarithms of these ratios) of native to perturbed gene expression levels are measured. In general, expression profiles and protein activity sampling will preferably be roughly three samples per decade of perturbation. For example, preferably seven or more perturbation parameter values are used to cover two decades in parameter value. Further, the perturbation control levels are preferably chosen so that five or more, or more preferably ten or more, perturbation control levels are present in the region where the characteristics of the cellular constituents rapidly change from native levels to saturation levels.

In the following, the variable "p" refers generally to perturbation control levels, which are preferably expressed as %-protein activity. The variable "R" refers generally to the perturbation response data. In detail, the l'th perturbation control level is referred to as "p". The perturbation response for the k'th cellular constituent is $R_k$. Therefore, $R_k(p_l)$ is the response of the k'th cellular constituent at the l'th level of the perturbation control parameter.

Similarly, diagnostic profile data are obtained in step 302, and must be measured if not already available. As described above, the data are obtained by measuring levels of cellular constituents in a cell of interest, i.e., a cell for which one wishes to determine the protein activity level of a particular protein. The actual protein activity level, p, is usually unknown when this data is acquired. In the following, the variable "D" refers generally to the diagnostic profile data. In detail, the diagnostic profile for the k'th cellular constituent is $D_k$. Therefore, $D_k(p)$ is the diagnostic profile of the k'th cellular constituent of a cell with the protein activity level, p. Typically, the values of $R_k(p)$ and $D_k$ are $\log_{10}$ of the expression ratio of each cellular constituent. The expression ratio is the ratio between the level in the perturbed or drug-treated system, and the level in the wild type or untreated system.

In general, the actual protein activity level at which diagnostic profile data are acquired will not correspond to any of the perturbation control levels at which perturbation response profiles are actually acquired. Accordingly, it is necessary in step 303 to provide for interpolating of the perturbation response data to obtain needed values. This interpolation method is preferably accomplished either by spline fitting or by model-fitting. The selection of an interpolation method and any necessary parameters is accomplished in step 303.

In spline fitting, the perturbation response data are interpolated by summing products of an appropriate spline interpolation function, S, multiplied by the measured data values, as illustrated by the following equation.

$$R_k(u) = \sum_l S(u - p_l) R_k(p_l) \tag{1}$$

The variable "u" refers to an arbitrary value of protein activity level at which the perturbation response data are to be evaluated. In general, S may be any smooth, or at least piece-wise continuous, function of limited support having a width characteristic of the structure expected in the response functions. An exemplary width can be chosen to be the distance over which the response function being interpolated rises from 10% to 90% of its asymptotic value. Exemplary S functions include linear and Gaussian interpolation.

In model fitting, the perturbation responses are interpolated by approximating each by a single parameterized function. An exemplary model-fitting function appropriate for approximating transcriptional state data is the Hill function, which has adjustable parameters a, $u_0$ and n.

$$H(u) = \frac{a(u/u_0)^n}{1 + (u/u_0)^n} \tag{2}$$

the adjustable parameters are selected independently for each cellular constituent of the perturbation response.

Preferably, the adjustable parameters are selected so that for each cellular constituent the sum of the squares of the distances $H(p_l)$ from $R_k(p_l)$ is minimized. This preferable parameter adjustment method is known in the art as a least squares fit of H( ) to $R_k$( ). Other possible model functions are based on polynomial fitting, for example by various known classes of polynomials.

Figure 4:
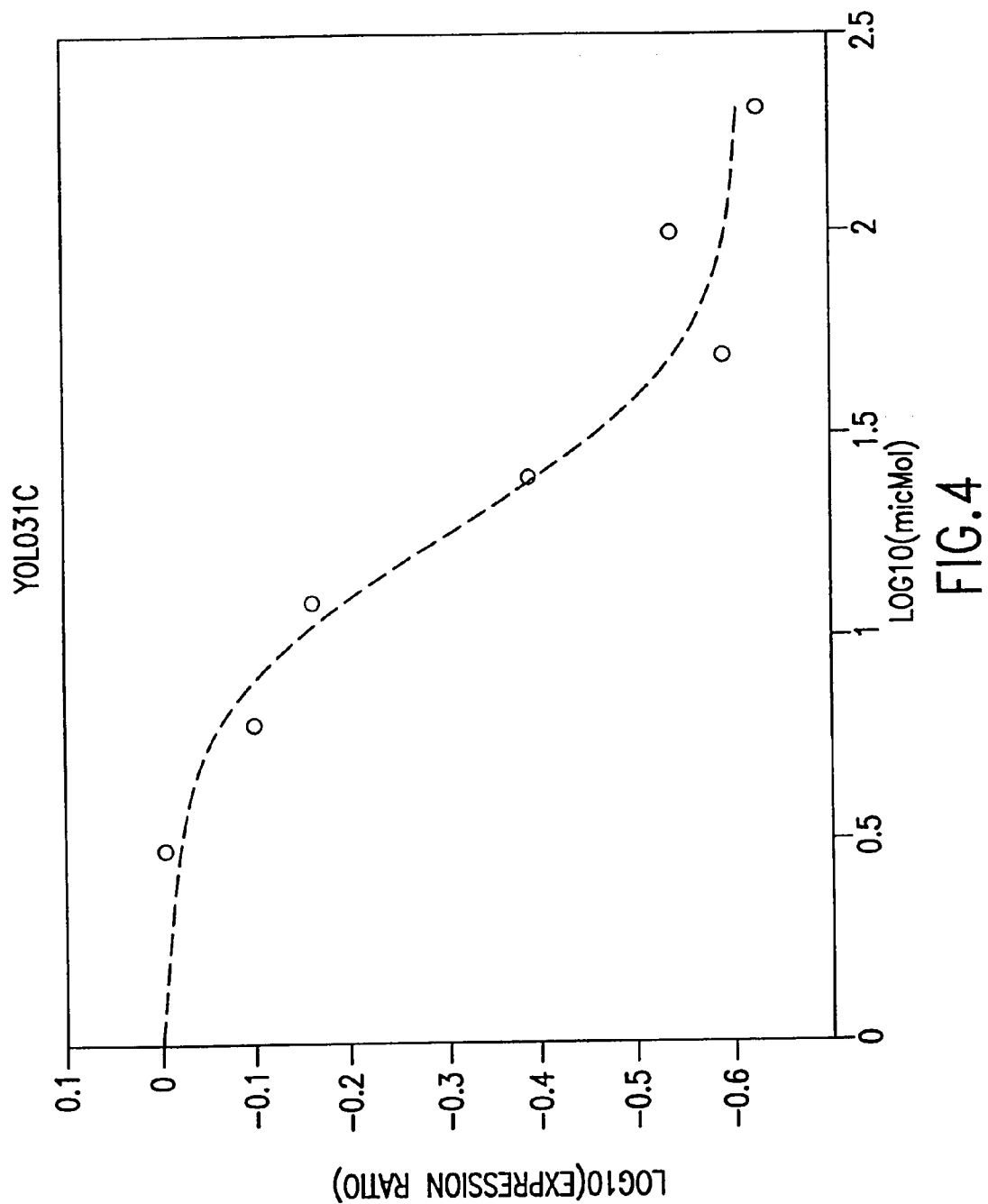
FIG. 4 illustrates the fit of a Hill function to the response of gene YOL031C illustrated in FIG. 2.

Model fitting with a Hill function is illustrated with respect to FIGS. 2 and 4. As discussed, FIG. 2 illustrates an example of perturbation by methotrexate and identified by measurement. This figure illustrates the RNA expression levels of 30 genes of the yeast *S. cerevisiae* that, of the approximately 6000 genes in the genome of this organism, had the largest expression changes in response to six different exposure levels of methotrexate. FIG. 4 illustrates a fit of the perturbation response of one of these gene expression levels by a Hill function. In particular, the yeast gene YOL031C was fit by a Hill function with parameters n=2, a=−0.61, and $\log_{10}(u_0)$=1.26 selected by the previously described least squares method.

Since all of the 30 genes with largest responses behaved monotonically, i.e., none of the responses decreased significantly from its maximum amplitude (or increased significantly from its minimum amplitude) with increasing drug exposure, the Hill function is an appropriate model fitting function. For non-monotonic behavior it would not be.

Given the interpolation of the perturbation responses to any value of protein activity, denoted p, the diagnostic expression profile D can be compared with the perturbation response curves R(p) to find the best-fit over all possible values of p. According to one preferred method, the best-fit over all possible values of p is determined from the minimization of the related least squares approximation problem.

$$\min_{\{p\}} \left\{ \sum_k (R_k(p) - D_k)^2 \right\} \tag{3}$$

In Eqn. 3, the absolute square of the difference of the interpolated response profile and the diagnostic profile is summed over all cellular constituents in the profiles, indexed by "k". The best-fit of the diagnostic profile in terms of the response curves is determined from the minimization of this sum with respect to the protein activity level p. Minimization of least squares Eqn. 3 is performed using any of the many available numerical methods. See, e.g., Press et al., 1996, *Numerical Recipes in C*, 2nd Ed. Cambridge Univ. Press, Chs. 10, 14.; Branch et al., 1996, *Matlab Optimization Toolbox User's Guide*, Mathworks (Natick, Mass.).

Typically, there will be some variation from experiment to nominally repeated experiment in the asymptotic value of the responses. Individual cellular constituents have similar relative response amplitudes in repeated experiment, but all responses may be systematically larger or smaller in one experiment. This can cause the value of p determined in Eqn. 3 to be biased high or low. An alternative fitting approach which prevents these systematic amplitude discrepancies from biasing the derived p is to maximize the correlation between the diagnostic perturbation response profile and the diagnostic profile. This procedure is closely related mathematically to the least squares procedure. According to this procedure, the protein activity level p is determined from the solution to Eqn. 4.

$$\max_{\{p\}} \left\{ \frac{\sum_k R_k(p) D_k}{\left[ \left( \sum_k R_k^2(p) \right) \left( \sum_k D_k^2 \right) \right]^{1/2}} \right\} \tag{4}$$

Eqn. 4 can be solved by the methods described in the case of the least squares methods. It will be clear to those killed in the art that the above fitting approach is equivalent to minimizing the negative value of Eqn. 4.

In certain instances, Eqn. 4 will have a very shallow, and hence poorly determined maximum location. Specifically, in many cases the response profiles R(p) will look very similar at different p except for an over-all scaling with increasing p. In these cases, the best-fit over all possible values of p is preferably determined by the least-squares method in Eqn. 3. In instances where the relative response amplitudes of different cellular constituents change significantly with changing protein activity, such as, for example, the response curves illustrated in FIG. 2, the best-fit over all possible values of p is preferably determined by maximizing Eqn. 4.

In specific embodiments, the methods of the invention can be used to determine the activity levels of a plurality of proteins in a cell. In such embodiments, the perturbation response profile, $R_{i,k}(p_{i,l})$ of the k'th cellular constituent at the l'th perturbation level is separately determined for the i'th protein. The perturbation response profiles for each protein are interpolated, as described above, to generate an interpolated response profile for each protein whose activity level is to be determined, $R_{i,k}(p_i)$. The diagnostic expression profile D can then be compared to a combination of the perturbation response curves $R_i(p_i)$ for each protein to find a best-fit over all possible values of $\{p_i\}$.

In a particularly preferred embodiment, the effects of therapies and/or the levels of dieases are sufficiently low that nonlinear or feed back effects, discussed above, are not observed. In such an embodiment, the perturbation response profile may simply be compared to the sum of perturbation response curves for each protein, i.e., to $\Sigma R_j(p_i)$. Accordingly, in embodiments where the best fit is determined by minimization of the least squares problem, the best fit is the solution to Eqn. 5.

$$\min_{\{p_i\}} \left\{ \sum_k \left( D_k - \sum_i R_{i,k}(p_i) \right)^2 \right\} \quad (5)$$

5.3.2. Assessing Statistical Significance

Following the extraction of a perturbation response profile which best fits the diagnostic profile, it is preferable, although optional, in certain embodiments to assign a statistical significance to the corresponding fit.

The statistical significance of the fit of a response profile to the diagnostic profile is determined by comparing the value of the minimum residual determined from the solution of Eqn. 3 to an expected probability distribution of residuals. The less likely the minimum residual is in terms of such a distribution, the more significant is the corresponding fit. In the case of the correlation maximization method, the same methods can be applied to the maximum found in Eqn. 4. In particular, an expected distribution of maximums can be found (as described below), and the significance of the actually obtained maximum determined from this distribution.

An expected probability distribution of residuals can be estimated by any method known in the art. Typically, this distribution is estimated analytically based on certain a priori assumptions concerning input probability distributions. Since such analytic estimation is difficult in this case, it is preferable to estimate the residual distribution by modeling based on a method described by Fisher. See, e.g., Conover, 2nd ed. 1980, *Practical Nonparametric Statistics*, John Wiley. This method provides an empirical residual distribution by taking permutations or random subsets of the input data. In detail, here the input can be permuted with respect to the cellular constituents measured in the diagnostic profile.

According to the preferred method, a residual distribution is constructed by repetitively solving Eqn. 3 (or Eqn. 4) with randomized input data and accumulating the residuals to form the empirical residual distribution.

Thereby, the constructed empirical residual distribution arises from random data that has the same population statistics as the actual data. In detail, first, either the diagnostic profile data or the response profile data (but not both) are randomized with respect to the cellular constituent index. This randomization transformation is represented by the following transformation.

$$D_k \leftarrow D_{\Pi(k)} \quad (6)$$
$$R_k(p_1) \leftarrow R_{\Pi(k)}(p_1)$$

In Eqn. 6, $\pi$ represents a perturbation independently chosen for each profile. Either the diagnostic profile or each response profile (but not both) is randomized according to Eqn. 6. Accordingly, the randomized expression profile data are derived from the measured data by independent permutations of the measurement points. Second, Eqn. 3 (or Eqn. 4) is then solved by the chosen numerical approximation technique and the value of the resulting residual saved. These steps are repeated for enough randomizations to construct a sufficiently significant expected probability distribution of residuals. In order to obtain confidence levels of 99% or better (i.e., a P-value less than 0.01), then more than 100 randomizations are needed.

Having constructed the empirical residual distribution, the actually determined residual is compared to the constructed distribution, and its probability determined in view of that distribution. This probability is the significance assigned to the fit of the extracted response profile to the diagnostic profile. In other words, the statistical significance of any fit of a combination of cellular constituents to the diagnostic profile is given in the preferred embodiment by the smallness of the probability value that randomized data are fit better by the assumed protein activity level than the actual data.

In cases wherein the fit has at least the standard 95% probability threshold commonly used in medical sciences, the corresponding protein activity level can then be considered to have adequate statistical significance. In other cases, an acceptable significance threshold may not be met. If so, then in certain embodiments it can be advantageous to select new perturbation profile data, preferably for a different protein, in order to find a response profile which fits the diagnostic profile with the chosen threshold of significance.

For example, in embodiments of this invention wherein the methods are used to identify individuals having genetic mutations or polymorphisms, the perturbation response profile data frequently consists of expression profile data from individuals having known protein perturbations due to drug treatment or genetic mutations. In such embodiments, it is preferable to assign a statistical significance to the fit of the perturbation response profile for the known protein perturbations to the diagnostic profile of an uncharacterized individual. In cases wherein the fit has at least the standard 95% probability threshold commonly used in medical sciences, the individual can then be diagnosed as having the corresponding known genetic mutation. Alternatively, if the fit does not have at least 95% significance, a statistical significance may be assigned to fits of one or more other perturbation response profiles to the diagnostic profile, using perturbation response profiles obtained from individuals having other, different, known protein perturbations until a perturbation response profile is identified which does have at least 95% significance.

5.3.3. Implementation Systems and Methods

Figure 5:
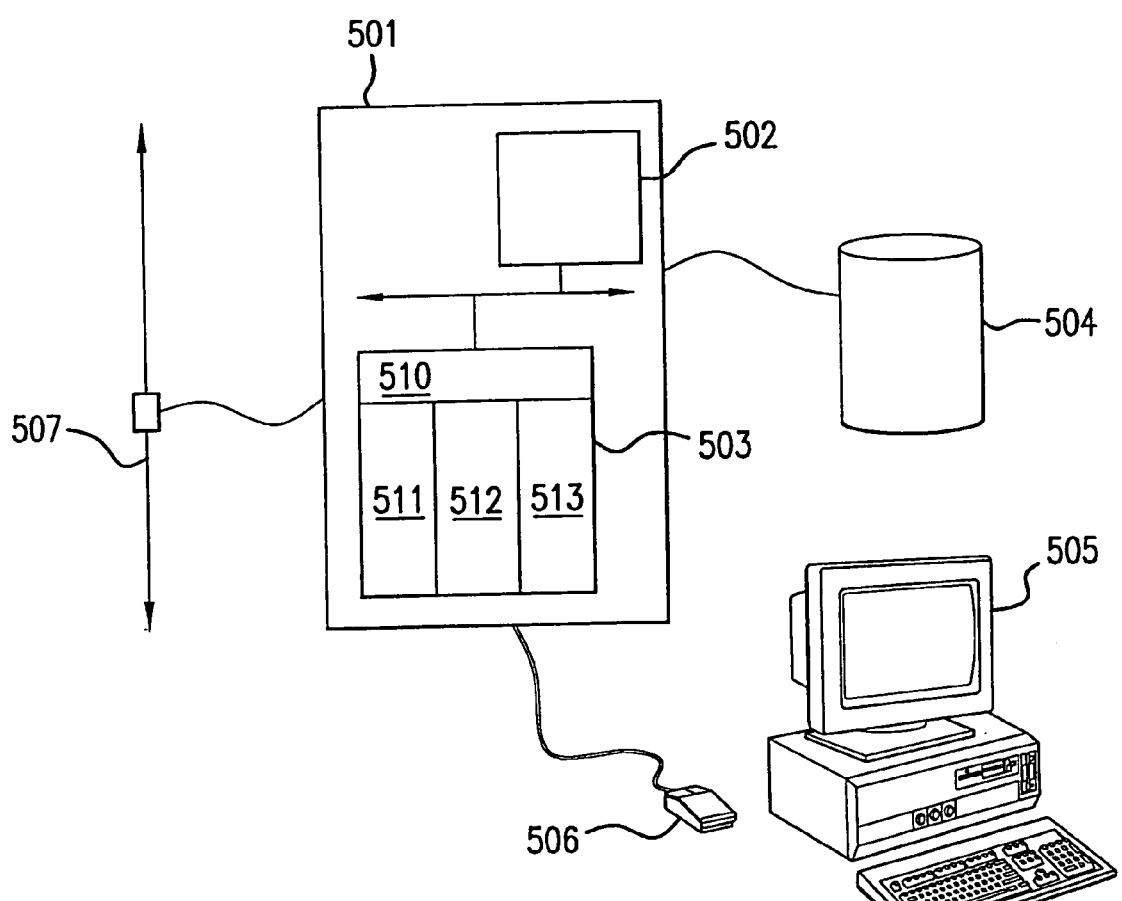
FIG. 5 illustrates an exemplary embodiment of a computer system of this invention.

The analytic methods described in the previous subsections can preferably be implemented by use of the following computer systems and according to the following programs and methods. FIG. 5 illustrates an exemplary computer system suitable for implementation of the analytic methods of this invention. Computer system 501 is illustrated as comprising internal components and being linked to external components. The internal components of this computer system include processor element 502 interconnected with main memory 503. For example, computer system 501 can be an Intel Pentium®-based processor of 200 Mhz or greater clock rate and with 32 MB or more of main memory.

The external components include mass storage 504. This mass storage can be one or more hard disks (which are typically packaged together with the processor and memory). Such hard disks are typically of 1 GB or greater storage capacity. Other external components include user interface device 505, which can be a monitor and keyboard, together with pointing device 506, which can be a "mouse", or other graphic input devices (not illustrated). Typically, computer system 501 is also linked to network link 507, which can be part of an Ethernet link to other local computer systems, remote computer systems, or wide area communication networks, such as the Internet. This network link allows computer system 501 to share data and processing tasks with other computer systems.

Loaded into memory during operation of this system are several software components, which are both standard in the art and special to the instant invention. These software components collectively cause the computer system to function according to the methods of this invention. These software components are typically stored on mass storage 504.

Software component 510 represents the operating system, which is responsible for managing computer system 501 and its network interconnections. This operating system can be, for example, of the Microsoft Windows™ family, such as Windows 95, Windows 98, or Windows NT. Software component 511 represents common languages and functions conveniently present on this system to assist programs implementing the methods specific to this invention. Languages that can be used to program the analytic methods of this invention include C and C++, or, less preferably, JAVA®. Most preferably, the methods of this invention are programmed in mathematical software packages which allow symbolic entry of equations and high-level specification of processing, including algorithms to be used, thereby freeing a user of the need to procedurally program individual equations or algorithms. Such packages include Matlab from Mathworks (Natick, Mass.), Mathematica from Wolfram Research (Champaign, Ill.), or S-Plus from Math Soft (Seattle, Wash.). Accordingly, software component 512 represents the analytic methods of this invention as programmed in a procedural language or symbolic package. In a preferred embodiment, the computer system also contains a database 513 of perturbation response curves for the particular protein. More preferably, the database 513 contains perturbation response curves for several proteins.

In an exemplary implementation, to practice the methods of the present invention, a user first loads diagnostic profile data into the computer system 501. These data can be directly entered by the user from monitor and keyboard 505, or from other computer systems linked by network connection 507, or on removable storage media such as a CD-ROM or floppy disk (not illustrated). Next the user causes execution of expression profile analysis software 512 which performs the steps of determining and minimizing an objective function of the difference between the diagnostic profile and a response profile determined from the perturbation response curves data for some protein activity level. In a less preferable embodiment, the user loads perturbation response profile data and the steps of interpolating the response profile data to generate perturbation response curves are performed by the analysis software 512.

The present invention also provides databases of perturbation response curves for use in determining protein activity levels according to the methods of this invention. The databases of this invention include perturbation response curves for a protein, preferably for several different proteins so that the same database may be used to determine protein activity levels for several different proteins. Preferably, such a database will be in an electronic form that can be loaded into a computer system such as the one illustrated in FIG. 5 and described supra. Such electronic forms include databases loaded into the main memory 503 of a computer system used to implement the methods of this invention, or in the main memory of other computers linked by network connection 507, or on mass storage media 504, or on removable storage media such as a CD-ROM or floppy disk.

In a preferred embodiment, the analytic methods of this invention can be implemented by use of kits for determining the activity level of a particular protein in a cell. Such kits contain microarrays, such as those described in Subsection 5.5.1, below. The microarrays contained in such kits comprise a solid phase, e.g., a surface, to which probes are hybridized or bound at a known location of the solid phase. Preferably, these probes consist of nucleic acids of known, different sequence, with each nucleic acid being capable of hybridizing to an RNA species or to a cDNA species derived therefrom. In particular, the probes contained in the kits of this invention are nucleic acids capable of hybridizing specifically to nucleic acid sequences derived from RNA species which are known to increase or decrease in response to perturbations to the particular protein whose activity is determined by the kit. The probes contained in the kits of this invention preferably substantially exclude nucleic acids which hybridize to RNA species that are not increased in response to perturbations to the particular protein whose activity is determined by the kit.

In a preferred embodiment, a kit of the invention also contains a database of perturbation response profiles such as the databases described above in this subsection.

In another preferred embodiment, a kit of the invention further contains expression profile analysis software capable of being loaded into the memory of a computer system such as the one described supra in the subsection, and illustrated in FIG. 5. The expression profile analysis software contained in the kit of this invention, is essentially identical to the expression profile analysis software 512 described above. Such software is capable of executing the analytical steps of the present invention. Preferably, the software causes the processor of a computer system to execute the steps of (a) receiving a diagnostic profile of a cell of said cell type, (b) receiving perturbation response curves for a protein of said cell type, and (c) determining the level of perturbation to said protein at which similarity is greatest between said diagnostic profile and the perturbation response profile extracted from said perturbation response curves.

Alternative systems and methods for implementing the analytic methods of this invention will be apparent to one of skill in the art and are intended to be comprehended within the accompanying claims. In particular, the accompanying claims are intended to include the alternative program structures for implementing the methods of this invention that will be readily apparent to one of skill in the art.

5.4. Protein Perturbation Methods

Methods for targeted perturbation of protein activity levels in a cell are increasingly widely known and applied in the art. Any such methods that are capable of specifically targeting and controllably modifying (e.g., either by a graded increase or activation or by a graded decrease or inhibition) specific cellular constituents (e.g., gene expression, RNA concentrations, protein abundances, protein activities, or so forth) can be employed in performing such perturbations. Preferable modification methods are capable of individually targeting each of a plurality of cellular constituents and most preferably a substantial fraction of such cellular constituents.

The following methods are exemplary of those that can be used to modify cellular constituents and thereby to produce perturbations in protein activity levels which generate the response profiles used in the steps of the methods of this invention as previously described. This invention is adaptable to other methods for making controllable perturbations to protein activity levels.

Perturbations to protein activity are preferably made in cells of cell types derived from any organism for which genomic or expressed sequence information is available and for which methods are available that permit controllable modification of the expression of specific genes. Genome sequencing is currently underway for several eukaryotic organisms, including humans, nematodes, Arabidopsis, and flies. In a preferred embodiment, the invention is carried out using a yeast, with *Saccharomyces cerevisiae* most preferred because the sequence of the entire genome of a *S. cerevisiae* strain has been determined. In addition, well-established methods are available for controllably modifying expression of yeast genes. A preferred strain of yeast is a *S. cerevisiae* strain for which yeast genomic sequence is known, such as strain S288C or substantially isogeneic derivatives of it (see, e.g., *Nature* 369, 371–8 (1994); *P.N.A.S.* 92:3809–13 (1995); *E.M.B.O. J.* 13:5795–5809 (1994), *Science* 265: 2077–2082 (1994); *E.M.B.O. J.* 15:2031–49 (1996), all of which are incorporated herein. However, other strains may be used as well. Yeast strains are available from American Type Culture Collection, Rockville, Md. 20852. Standard techniques for manipulating yeast are described in C. Kaiser, S. Michaelis, & A. Mitchell, 1994, *Methods in Yeast Genetics: A Cold Spring Harbor Laboratory Course Manual*, Cold Spring Harbor Laboratory Press, New York; and Sherman et al., 1986, *Methods in Yeast Genetics*: A Laboratory Manual, Cold Spring Harbor Laboratory, Cold Spring Harbor. N.Y., both of which are incorporated by reference in their entirety and for all purposes.

The exemplary methods described in the following include use of titratable expression systems, use of transfection or viral transduction systems, direct modifications to RNA abundances or activities, direct modifications of protein abundances, and direct modification of protein activities including use of drugs (or chemical moieties in general) with specific known action.

Titratable Expression Systems

Any of the several known titratable, or equivalently controllable, expression systems available for use in the budding yeast *Saccharomyces cerevisiae* are adaptable to this invention (Mumberg et al., 1994, Regulatable promoter of *Saccharomyces cerevisiae*: comparison of transcriptional activity and their use for heterologous expression, Nucl. Acids Res. 22:5767–5768). Usually, gene expression is controlled by transcriptional controls, with the promoter of the gene to be controlled replaced on its chromosome by a controllable, exogenous promoter. The most commonly used controllable promoter in yeast is the GAL1 promoter (Johnston et al., 1984, Sequences that regulate the divergent GAL1-GAL10 promoter in *Saccharomyces cerevisiae*, Mol Cell. Biol. 8:1440–1448). The GAL1 promoter is strongly repressed by the presence of glucose in the growth medium, and is gradually switched on in a graded manner to high levels of expression by the decreasing abundance of glucose and the presence of galactose. The GAL1 promoter usually allows a 5–100 fold range of expression control on a gene of interest.

Other frequently used promoter systems include the MET25 promoter (Kerjan et al., 1986, Nucleotide sequence of the *Saccharomyces cerevisiae* MET25 gene, Nucl. Acids. Res. 14:7861–7871), which is induced by the absence of methionine in the growth medium, and the CUP1 promoter, which is induced by copper (Mascorro-Gallardo et al., 1996, Construction of a CUP1 promoter-based vector to modulate gene expression in *Saccharomyces cerevisiae*, Gene 172: 169–170). All of these promoter systems are controllable in that gene expression can be incrementally controlled by incremental changes in the abundances of a controlling moiety in the growth medium.

One disadvantage of the above listed expression systems is that control of promoter activity (effected by, e.g., changes in carbon source, removal of certain amino acids), often causes other changes in cellular physiology which independently alter the expression levels of other genes. A recently developed system for yeast, the Tet system, alleviates this problem to a large extent (Gari et al., 1997, A set of vectors with a tetracycline-regulatable promoter system for modulated gene expression in *Saccharomyces cerevisiae*, Yeast 13:837–848). The Tet promoter, adopted from mammalian expression systems (Gossen et al., 1995, Transcriptional activation by tetracyclines in mammalian cells, Proc. Natl. Acad. Sci. USA 89:5547–5551) is modulated by the concentration of the antibiotic tetracycline or the structurally related compound doxycycline. Thus, in the absence of doxycycline, the promoter induces a high level of expression, and the addition of increasing levels of doxycycline causes increased repression of promoter activity. Intermediate levels of gene expression can be achieved in the steady state by addition of intermediate levels of drug. Furthermore, levels of doxycycline that give maximal repression of promoter activity (10 micrograms/ml) have no significant effect on the growth rate on wild type yeast cells (Gari et al., 1997, A set of vectors with a tetracycline-regulatable promoter system for modulated gene expression in *Saccharomyces cerevisiae*, Yeast 13:837–848).

In mammalian cells, several means of titrating expression of genes are available (Spencer, 1996, Creating conditional mutations in mammals, Trends Genet. 12:181–187). As mentioned above, the Tet system is widely used, both in its original form, the "forward" system, in which addition of doxycycline represses transcription, and in a newer "reverse" system, in which doxycycline addition stimulates transcription (Gossen et al., 1995, Proc. Natl. Acad. Sci. USA 89:5547–5551; Hoffmann et al., 1997, Nucl. Acids. Res. 25:1078–1079; Hofmann et al., 1996, Proc. Natl. Acad. Sci. USA 83:5185–5190; Paulus et al., 1996, Journal of Virology 70:62–67). Another commonly used controllable promoter system in mammalian cells is the ecdysone-inducible system developed by Evans and colleagues (No et al., 1996, Ecdysone-inducible gene expression in mammalian cella and transgenic mice, Proc. Natl. Acad. Sci. USA 93:3346–3351), where expression is controlled by the level of muristerone added to the cultured cells. Finally, expression can be modulated using the "chemical-induced dimerization" (CID) system developed by Schreiber, Crabtree, and colleagues (Belshaw et al., 1996, Controlling protein association and subcellular localization with a synthetic ligand that induces heterodimerization of proteins, Proc. Natl. Acad. Sci. USA 93:4604–4607; Spencer, 1996, Creating conditional mutations in mammals, Trends Genet.

12:181–187) and similar systems in yeast. In this system, the gene of interest is put under the control of the CID-responsive promoter, and transfected into cells expressing two different hybrid proteins, one comprised of a DNA-binding domain fused to FKBP12, which binds FK506. The other hybrid protein contains a transcriptional activation domain also fused to FKBP12. The CID inducing molecule is FK1012, a homodimeric version of FK506 that is able to bind simultaneously both the DNA binding and transcriptional activating hybrid proteins. In the graded presence of FK1012, graded transcription of the controlled gene is activated.

For each of the mammalian expression systems described above, as is widely known to those of skill in the art, the gene of interest is put under the control of the controllable promoter, and a plasmid harboring this construct along with an antibiotic resistance gene is transfected into cultured mammalian cells. In general, the plasmid DNA integrates into the genome, and drug resistant colonies are selected and screened for appropriate expression of the regulated gene. Alternatively, the regulated gene can be inserted into an episomal plasmid such as pCEP4 (Invitrogen, Inc.), which contains components of the Epstein-Barr virus necessary for plasmid replication.

In a preferred embodiment, titratable expression systems, such as the ones described above, are introduced for use into cells or organisms lacking the corresponding endogenous gene and/or gene activity, e.g., organisms in which the endogenous gene has been disrupted or deleted. Methods for producing such "knock outs" are well known to those of skill in the art, see e.g., Pettitt et al., 1996, Development 122: 4149–4157; Spradling et al., 1995, Proc. Natl. Acad. Sci. USA, 92:10824–10830; Ramirez-Solis et al., 1993, Methods Enzymol. 225:855–878; and Thomas et al., 1987, Cell 51:503–512.

Transfection Systems for Mammalian Cells

Transfection or viral transduction of target genes can introduce controllable perturbations in protein activity levels in mammalian cells. Preferably, transfection or transduction of a target gene can be used with cells that do not naturally express the target gene of interest. Such non-expressing cells can be derived from a tissue not normally expressing the target gene or the target gene can be specifically mutated in the cell. The target gene of interest can be cloned into one of many mammalian expression plasmids, for example, the pcDNA3.1 +/− system (Invitrogen, Inc.) or retroviral vectors, and introduced into the non-expressing host cells. Transfected or transduced cells expressing the target gene may be isolated by selection for a drug resistance marker encoded by the expression vector. The level of gene transcription is monotonically related to the transfection dosage. In this way, the effects of varying levels of the target gene may be investigated.

A particular example of the use of this method is the search for drugs that target the src-family protein tyrosine kinase, lck, a key component of the T cell receptor activation pathway (Anderson et al., 1994, Involvement of the protein tyrosine kinase p56 (lck) in T cell signaling and thymocyte development, Adv. Immunol. 56:171–178). Inhibitors of this enzyme are of interest as potential immunosuppressive drugs (Hanke J H, 1996, Discovery of a Novel, Potent, and src family-selective tyrosine kinase inhibitor, J. Biol Chem 271(2):695–701). A specific mutant of the Jurkat T cell line (JcaM1) is available that does not express lck kinase (Straus et al., 1992, Genetic evidence for the involvement of the lck tyrosine kinase in signal transduction through the T cell antigen receptor, Cell 70:585–593). Therefore, introduction of the lck gene into JCaM1 by transfection or transduction permits specific perturbation of pathways of T cell activation regulated by the lck kinase. The efficiency of transfection or transduction, and thus the level of perturbation, is dose related. The method is generally useful for providing perturbations of gene expression or protein abundances in cells not normally expressing the genes to be perturbed.

Methods of Modifying RNA Abundances or Activities

Methods of modifying RNA abundances and activities currently fall within three classes, ribozymes, antisense species, and RNA aptamers (Good et al., 1997, Gene Therapy 4: 45–54). Controllable application or exposure of a cell to these entities permits controllable perturbation of RNA abundances.

Ribozymes are RNAs which are capable of catalyzing RNA cleavage reactions. (Cech, 1987, Science 236:1532–1539; PCT International Publication WO 90/11364, published Oct. 4, 1990; Sarver et al., 1990, Science 247: 1222–1225). "Hairpin" and "hammerhead" RNA ribozymes can be designed to specifically cleave a particular target mRNA. Rules have been established for the design of short RNA molecules with ribozyme activity, which are capable of cleaving other RNA molecules in a highly sequence specific way and can be targeted to virtually all kinds of RNA. (Haseloff et al., 1988, Nature 334: 585–591; Koizumi et al., 1988, FEES Lett., 228:228–230; Koizumi et al., 1988, FEBS Lett., 239:285–288). Ribozyme methods involve exposing a cell to, inducing expression in a cell, etc. of such small RNA ribozyme molecules. (Grassi and Marini, 1996, Annals of Medicine 28: 499–510; Gibson, 1996, Cancer and Metastasis Reviews 15: 287-299).

Ribozymes can be routinely expressed in vivo in sufficient number to be catalytically effective in cleaving mRNA, and thereby modifying mRNA abundances in a cell. (Cotten et al., 1989, Ribozyme mediated destruction of RNA in vivo, The EMBO J. 8:3861–3866). In particular, a ribozyme coding DNA sequence, designed according to the previous rules and synthesized, for example, by standard phosphoramidite chemistry, can be ligated into a restriction enzyme site in the anticodon stem and loop of a gene encoding a tRNA, which can then be transformed into and expressed in a cell of interest by methods routine in the art. Preferably, an inducible promoter (e.g., a glucocorticoid or a tetracycline response element) is also introduced into this construct so that ribozyme expression can be selectively controlled. tDNA genes (i.e., genes encoding tRNAs) are useful in this application because of their small size, high rate of transcription, and ubiquitous expression in different kinds of tissues. Therefore, ribozymes can be routinely designed to cleave virtually any mRNA sequence, and a cell can be routinely transformed with DNA coding for such ribozyme sequences such that a controllable and catalytically effective amount of the ribozyme is expressed. Accordingly the abundance of virtually any RNA species in a cell can be perturbed.

In another embodiment, activity of a target RNA (preferable mRNA) species, specifically its rate of translation, can be controllably inhibited by the controllable application of antisense nucleic acids. An "antisense" nucleic acid as used herein refers to a nucleic acid capable of hybridizing to a sequence-specific (e.g., non-poly A) portion of the target RNA, for example its translation initiation region, by virtue of some sequence complementarity to a coding and/or non-coding region. The antisense nucleic acids of the invention can be oligonucleotides that are double-stranded or single-stranded, RNA or DNA or a modification or derivative thereof, which can be directly administered in a controllable manner to a cell or which can be produced intracellularly by transcription of exogenous, introduced sequences in controllable quantities sufficient to perturb translation of the target RNA.

Preferably, antisense nucleic acids are of at least six nucleotides and are preferably oligonucleotides (ranging from 6 to about 200 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86: 6553–6556; Lemaitre et al., 1987, Proc. Natl. Acad. Sci. 84: 648–652; PCT Publication No. WO 88/09810, published Dec. 15, 1988), hybridization-triggered cleavage agents (see, e.g., Krol et al., 1988, BioTechniques 6: 958–976) or intercalating agents (see, e.g., Zon, 1988, Pharm. Res. 5: 539–549).

In a preferred aspect of the invention, an antisense oligonucleotide is provided, preferably as single-stranded DNA. The oligonucleotide may be modified at any position on its structure with constituents generally known in the art.

The antisense oligonucleotides may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the oligonucleotide comprises at least one modified sugar moiety selected from the group including, but not limited to, arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is a 2-α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15: 6625–6641).

The oligonucleotide may be conjugated to another molecule, e.g., a peptide, hybridization triggered cross-linking agent, transport agent, hybridization-triggered cleavage agent, etc.

The antisense nucleic acids used according to the invention comprise a sequence complementary to at least a sequence specific portion of a target RNA species. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a target RNA it may contain and still form a stable duplex (or triplex, as the case may be). One skilled in the art can ascertain a tolerable degree of mismatch by use of standard procedures to determine the melting point of the hybridized complex. The amount of antisense nucleic acid that will be effective in the inhibiting translation of the target RNA can be determined by standard assay techniques.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16: 3209), methylphosphonate oligonucleotides can be prepared by use of controlled pore glass polymer supports (Sarin et al., 1988, Proc. Natl. Acad. Sci. U.S.A. 85: 7448–7451), etc. In another embodiment, the oligonucleotide is a 2'-0-methylribonucleotide (Inoue et al., 1987, Nucl. Acids Res. 15: 6131–6148), or a chimeric RNA-DNA analog (Inoue et al., 1987, FEBS Lett. 215: 327–330).

The synthesized antisense oligonucleotides can then be administered to a cell in a controlled manner. For example, the antisense oligonucleotides can be placed in the growth environment of the cell at controlled levels where they may be taken up by the cell. The uptake of the antisense oligonucleotides can be assisted by use of methods well known in the art.

In an alternative embodiment, the antisense nucleic acids of the invention are controllably expressed intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequences encoding the antisense RNAs can be by any promoter known in the art to act in a cell of interest. Such promoters can be inducible or constitutive. Most preferably, promoters are controllable or inducible by the administration of an exogenous moiety in order to achieve controlled expression of the antisense oligonucleotide. Such controllable promoters include the Tet promoter. Less preferably usable promoters for mammalian cells include, but are not limited to: the SV40 early promoter region (Bernoist and Chambon, 1981, Nature 290: 304–310), the promoter contained in the 3' long terminal repeat of Rous sarcoma virus (Yamamoto et al., 1980, Cell 22: 787–797), the herpes thymidine kinase promoter (Wagner et al., 1981, Proc. Natl. Acad. Sci. U.S.A. 78: 1441–1445), the regulatory sequences of the metallothionein gene (Brinster et al., 1982, Nature 296: 39–42), etc.

Therefore, antisense nucleic acids can be routinely designed to target virtually any mRNA sequence, and a cell can be routinely transformed with or exposed to nucleic acids coding for such antisense sequences such that an effective and controllable amount of the antisense nucleic acid is expressed. Accordingly the translation of virtually any RNA species in a cell can be controllably perturbed.

Finally, in a further embodiment, RNA aptamers can be introduced into or expressed in a cell. RNA aptamers are specific RNA ligands for proteins, such as for Tat and Rev RNA (Good et al., 1997, Gene Therapy 4: 45–54) that can specifically inhibit their translation.

Methods of Modifying Protein Abundances

Methods of modifying protein abundances include, inter alia, those altering protein degradation rates and those using antibodies (which bind to proteins affecting abundances of activities of native target protein species). Increasing (or decreasing) the degradation rates of a protein species decreases (or increases) the abundance of that species. Methods for controllably increasing the degradation rate of a target protein in response to elevated temperature and/or exposure to a particular drug, which are known in the art, can be employed in this invention. For example, one such method employs a heat-inducible or drug-inducible N-terminal degron, which is an N-terminal protein fragment that exposes a degradation signal promoting rapid protein degradation at a higher temperature (e.g., 37° C.) and which is hidden to prevent rapid degradation at a lower temperature (e.g., 23° C.) (Dohmen et. al, 1994, Science 263:1273–1276). Such an exemplary degron is Arg-DHFR$^{ts}$, a variant of murine dihydrofolate reductase in which the N-terminal Val is replaced by Arg and the Pro at position 66 is replaced with Leu. According to this method, for example, a gene for a target protein, P, is replaced by standard gene targeting methods known in the art (Lodish et al., 1995, *Molecular Biology of the Cell*, W.H. Freeman and Co., New York, especially chap 8) with a gene coding for the fusion protein Ub-Arg-DHFR$^{ts}$-P ("Ub" stands for ubiquitin). The N-terminal ubiquitin is rapidly cleaved after translation exposing the N-terminal degron. At lower temperatures, lysines internal to Arg-DHFR$^{ts}$ are not exposed, ubiquitination of the fusion protein does not occur, degradation is slow, and active target protein levels are high. At higher temperatures (in the absence of methotrexate), lysines internal to Arg-DHFR$^{ts}$ are exposed, ubiquitination of the fusion protein occurs, degradation is rapid, and active target protein levels are low. Heat activation of degradation is controllably blocked by exposure methotrexate. This method is adaptable to other N-terminal degrons which are responsive to other inducing factors, such as drugs and temperature changes.

Target protein abundances and also, directly or indirectly, their activities can also be decreased by (neutralizing) antibodies. By providing for controlled exposure to such antibodies, protein abundances/activities can be controllably modified. For example, antibodies to suitable epitopes on protein surfaces may decrease the abundance, and thereby indirectly decrease the activity, of the wild-type active form of a target protein by aggregating active forms into complexes with less or minimal activity as compared to the wild-type unaggregated wild-type form. Alternately, antibodies may directly decrease protein activity by, e.g., interacting directly with active sites or by blocking access of substrates to active sites. Conversely, in certain cases, (activating) antibodies may also interact with proteins and their active sites to increase resulting activity. In either case, antibodies (of the various types to be described) can be raised against specific protein species (by the methods to be described) and their effects screened. The effects of the antibodies can be assayed and suitable antibodies selected that raise or lower the target protein species concentration and/or activity. Such assays involve introducing antibodies into a cell (see below), and assaying the concentration of the wild-type amount or activities of the target protein by standard means (such as immunoassays) known in the art. The net activity of the wild-type form can be assayed by assay means appropriate to the known activity of the target protein.

Antibodies can be introduced into cells in numerous fashions, including, for example, microinjection of antibodies into a cell (Morgan et al., 1988, Immunology Today 9:84–86) or transforming hybridoma mRNA encoding a desired antibody into a cell (Burke et al., 1984, Cell 36:847–858). In a further technique, recombinant antibodies can be engineering and ectopically expressed in a wide variety of non-lymphoid cell types to bind to target proteins as well as to block target protein activities (Biocca et al, 1995, Trends in Cell Biology 5:248–252). Preferably, expression of the antibody is under control of a controllable promoter, such as the Tet promoter. A first step is the selection of a particular monoclonal antibody with appropriate specificity to the target protein (see below). Then sequences encoding the variable regions of the selected antibody can be cloned into various engineered antibody formats, including, for example, whole antibody, Fab fragments, Fv fragments, single chain Fv fragments ($V_H$ and $V_L$ regions united by a peptide linker) ("ScFv" fragments), diabodies (two associated ScFv fragments with different specificities), and so forth (Hayden et al., 1997, Current Opinion in Immunology 9:210–212). Intracellularly expressed antibodies of the various formats can be targeted into cellular compartments (e.g., the cytoplasm, the nucleus, the mitochondria, etc.) by expressing them as fusions with the various known intracellular leader sequences (Bradbury et al., 1995, *Antibody Engineering* (vol. 2) (Borrebaeck ed.), pp 295–361, IRL Press). In particular, the ScFv format appears to be particularly suitable for cytoplasmic targeting.

Antibody types include, but are not limited to, polyclonal, monoclonal, chimeric, single chain, Fab fragments, and an Fab expression library. Various procedures known in the art may be used for the production of polyclonal antibodies to a target protein. For production of the antibody, various host animals can be immunized by injection with the target protein, such host animals include, but are not limited to, rabbits, mice, rats, etc. Various adjuvants can be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacillus Calmette-Guerin (BCG) and corynebacterium parvum.

For preparation of monoclonal antibodies directed towards a target protein, any technique that provides for the production of antibody molecules by continuous cell lines in culture may be used. Such techniques include, but are not restricted to, the hybridoma technique originally developed by Kohler and Milstein (1975, Nature 256: 495–497), the trioma technique, the human B-cell hybridoma technique (Kozbor et al., 1983, Immunology Today 4: 72), and the EBV hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. USA 80: 2026–2030), or by transforming human B cells with EBV virus in vitro (Cole et al., 1985, in Monoclonal Antibodies and Cancer Therapy, Alan R. Liss, Inc., pp. 77–96). In fact, according to the invention, techniques developed for the production of "chimeric antibodies" (Morrison et al., 1984, Proc. Natl. Acad. Sci. USA 81: 6851–6855; Neuberger et al., 1984, Nature 312:604–608; Takeda et al., 1985, Nature 314: 452–454) by splicing the genes from a mouse antibody molecule specific for the target protein together with genes from a human antibody molecule of appropriate biological activity can be used; such antibodies are within the scope of this invention.

Additionally, where monoclonal antibodies are advantageous, they can be alternatively selected from large antibody libraries using the techniques of phage display (Marks et al., 1992, J. Biol. Chem. 267:16007–16010). Using this technique, libraries of up to 1012 different antibodies have been expressed on the surface of fd filamentous phage, creating a "single pot" in vitro immune system of antibodies available for the selection of monoclonal antibodies (Griffiths et al., 1994, EMBO J. 13:3245–3260). Selection of antibodies from such libraries can be done by techniques known in the art, including contacting the phage to immobilized target protein, selecting and cloning phage bound to the target, and subcloning the sequences encoding the antibody variable regions into an appropriate vector expressing a desired antibody format.

According to the invention, techniques described for the production of single chain antibodies (U.S. Pat. No. 4,946,778) can be adapted to produce single chain antibodies specific to the target protein. An additional embodiment of the invention utilizes the techniques described for the construction of Fab expression libraries (Huse et al., 1989, Science 246: 1275–1281) to allow rapid and easy identification of monoclonal Fab fragments with the desired specificity for the target protein.

Antibody fragments that contain the idiotypes of the target protein can be generated by techniques known in the art. For example, such fragments include, but are not limited to: the F(ab')$_2$ fragment which can be produced by pepsin digestion of the antibody molecule; the Fab' fragments that can be generated by reducing the disulfide bridges of the F(ab')$_2$ fragment, the Fab fragments that can be generated by treating the antibody molecule with papain and a reducing agent, and Fv fragments.

In the production of antibodies, screening for the desired antibody can be accomplished by techniques known in the art, e.g., ELISA (enzyme-linked immunosorbent assay). To select antibodies specific to a target protein, one may assay generated hybridomas or a phage display antibody library for an antibody that binds to the target protein.

Methods of Modifying Protein Activities

Methods of directly modifying protein activities include, inter alia, dominant negative mutations, specific drugs (used in the sense of this application) or chemical moieties generally, and also the use of antibodies, as previously discussed.

Dominant negative mutations are mutations to endogenous genes or mutant exogenous genes that when expressed in a cell disrupt the activity of a targeted protein species. Depending on the structure and activity of the targeted protein, general rules exist that guide the selection of an appropriate strategy for constructing dominant negative mutations that disrupt activity of that target (Hershkowitz, 1987, Nature 329:219–222). In the case of active monomeric forms, overexpression of an inactive form can cause competition for natural substrates or ligands sufficient to significantly reduce net activity of the target protein. Such over expression can be achieved by, for example, associating a promoter, preferably a controllable or inducible promoter, of increased activity with the mutant gene. Alternatively, changes to active site residues can be made so that a virtually irreversible association occurs with the target ligand. Such can be achieved with certain tyrosine kinases by careful replacement of active site serine residues (Perlmutter et al., 1996, Current Opinion in Immunology 8:285–290).

In the case of active multimeric forms, several strategies can guide selection of a dominant negative mutant. Multimeric activity can be controllably decreased by expression of genes coding exogenous protein fragments that bind to multimeric association domains and prevent multimer formation. Alternatively, controllable over expression of an inactive protein unit of a particular type can tie up wild-type active units in inactive multimers, and thereby decrease multimeric activity (Nocka et al., 1990, The EMBO J. 9:1805-1813). For example, in the case of dimeric DNA binding proteins, the DNA binding domain can be deleted from the DNA binding unit, or the activation domain deleted from the activation unit. Also, in this case, the DNA binding domain unit can be expressed without the domain causing association with the activation unit. Thereby, DNA binding sites are tied up without any possible activation of expression. In the case where a particular type of unit normally undergoes a conformational change during activity, expression of a rigid unit can inactivate resultant complexes. For a further example, proteins involved in cellular mechanisms, such as cellular motility, the mitotic process, cellular architecture, and so forth, are typically composed of associations of many subunits of a few types. These structures are often highly sensitive to disruption by inclusion of a few monomeric units with structural defects. Such mutant monomers disrupt the relevant protein activities and can be controllably expressed in a cell.

In addition to dominant negative mutations, mutant target proteins that are sensitive to temperature (or other exogenous factors) can be found by mutagenesis and screening procedures that are well-known in the art.

Also, one of skill in the art will appreciate that expression of antibodies binding and inhibiting a target protein can be employed as another dominant negative strategy.

Drugs of Specific Known Action

Activities of certain target proteins can be controllably altered by exposure to exogenous drugs or ligands. In a preferable case, a drug is known that interacts with only one target protein in the cell and alters the activity of only that one target protein. Graded exposure of a cell to varying amounts of that drug thereby causes graded perturbations of pathways originating at that protein. The alteration can be either a decrease or an increase of activity. Less preferably, a drug is known and used that alters the activity of only a few (e.g., 2–5) target proteins with separate, distinguishable, and non-overlapping effects. Graded exposure to such a drug causes graded perturbations to the several pathways originating at the target proteins.

Heterozygous Mutations of Known Genes

As noted supra, there are a large number of proteins whose function critically affects specific physiological pathways. In situations where protein activity levels are disrupted by mutations that disrupt the activity of one of two alleles, it is possible to analyze the expression profiles from a series of individuals who have known heterozygous mutations in order to identify a response profile that could help identify uncharacterized individuals who carry the similar inactivating mutations.

5.5. Measurement Methods

Diagnostic and perturbation response profiles are obtained for use in the instant invention by measuring the cellular constituents changed by perturbation of the protein activity level. These cellular characteristics can be of any aspect of the biological state of a cell. They can be of the transcriptional state, in which RNA abundances are measured, the translation state, in which protein abundances are measured, the activity state, in which protein activities are measured. The cellular characteristics can also be of mixed aspects, for example, in which the activities of one or more proteins are measured along with the RNA abundances (gene expressions) of cellular constituents. This section describes exemplary methods for measuring the cellular constituents affected by disrupted or perturbed protein activity levels. This invention is adaptable to other methods of such measurement.

Embodiments of this invention based on measuring the transcriptional state of drug and pathway responses are preferred. The transcriptional state can be measured by techniques of hybridization to arrays of nucleic acid or nucleic acid mimic probes, described in the next subsection, or by other gene expression technologies, described in the subsequent subsection. However measured, the result is response data including values representing RNA abundance ratios, which usually reflect DNA expression ratios (in the absence of differences in RNA degradation rates). Such measurement methods are described in Section 5.5.1.

In various alternative embodiments of the present invention, aspects of the biological state other than the transcriptional state, such as the translational state, the activity state, or mixed aspects can be measured. Details of these embodiments are described in this section. Such measurement methods are described in Section 5.5.2.

5.5.1. Transcriptional State Measurement

Preferably, measurement of the transcriptional state is made by hybridization to transcript arrays, which are described in this subsection. Certain other methods of transcriptional state measurement are described later in this subsection.

Transcript Arrays Generally

In a preferred embodiment the present invention makes use of "transcript arrays" (also called herein "microarrays"). Transcript arrays can be employed for analyzing the transcriptional state in a cell, and especially for measuring the transcriptional states of a cells exposed to graded levels of a drug of interest or to graded perturbations to a biological pathway of interest.

In one embodiment, transcript arrays are produced by hybridizing detectably labeled polynucleotides representing the mRNA transcripts present in a cell (e.g., fluorescently labeled cDNA synthesized from total cell mRNA) to a microarray. A microarray is a surface with an ordered array of binding (e.g., hybridization) sites for products of many of the genes in the genome of a cell or organism, preferably most or almost all of the genes. Microarrays can be made in a number of ways, of which several are described below. However produced, microarrays share certain characteristics: The arrays are reproducible, allowing multiple copies of a given array to be produced and easily compared with each other. Preferably the microarrays are small, usually smaller than 5 cm$^2$, and they are made from materials that are stable under binding (e.g. nucleic acid hybridization) conditions. A given binding site or unique set of binding sites in the microarray will specifically bind the product of a single gene in the cell. Although there may be more than one physical binding site (hereinafter "site") per specific mRNA, for the sake of clarity the discussion below will assume that there is a single site.

It will be appreciated that when cDNA complementary to the RNA of a cell is made and hybridized to a microarray under suitable hybridization conditions, the level of hybridization to the site in the array corresponding to any particular gene will reflect the prevalence in the cell of mRNA transcribed from that gene. For example, when detectably labeled (e.g., with a fluorophore) cDNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

In preferred embodiments, cDNAs from two different cells are hybridized to the binding sites of the microarray. In the case of drug responses one cell is exposed to a drug and another cell of the same type is not exposed to the drug. In the case of pathway responses one cell is exposed to a pathway perturbation and another cell of the same type is not exposed to the pathway perturbation. The cDNA derived from each of the two cell types are differently labeled so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular mRNA detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the relative abundance of a particular mRNA in a cell, the mRNA will be equally prevalent in both cells and, upon reverse transcription, red-labeled and green-labeled cDNA will be equally prevalent. When hybridized to the microarray, the binding site(s) for that species of RNA will emit wavelengths characteristic of both fluorophores (and appear brown in combination). In contrast, when the drug-exposed cell is treated with a drug that, directly or indirectly, increases the prevalence of the mRNA in the cell, the ratio of green to red fluorescence will increase. When the drug decreases the mRNA prevalence, the ratio will decrease.

The use of a two-color fluorescence labeling and detection scheme to define alterations in gene expression has been described, e.g., in Shena et al., 1995, Quantitative monitoring of gene expression patterns with a complementary DNA microarray, Science 270:467–470, which is incorporated by reference in its entirety for all purposes. An advantage of using cDNA labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular mRNA in, e.g., a drug-treated or pathway-perturbed cell and an untreated cell.

Preparation of Microarrays

Microarrays are known in the art and consist of a surface to which probes that correspond in sequence to gene products (e.g., cDNAs, mRNAs, cRNAs, polypeptides, and fragments thereof), can be specifically hybridized or bound at a known position. In one embodiment, the microarray is an array (i.e., a matrix) in which each position represents a discrete binding site for a product encoded by a gene (e.g., a protein or RNA), and in which binding sites are present for products of most or almost all of the genes in the organism's genome. In a preferred embodiment, the "binding site" (hereinafter, "site") is a nucleic acid or nucleic acid analogue to which a particular cognate cDNA can specifically hybridize. The nucleic acid or analogue of the binding site can be, e.g., a synthetic oligomer, a full-length cDNA, a less-than full length cDNA, or a gene fragment.

Although in a preferred embodiment the microarray contains binding sites for products of all or almost all genes in the target organism's genome, such comprehensiveness is not necessarily required. Usually the microarray will have binding sites corresponding to at least about 50% of the genes in the genome, often at least about 75%, more often at least about 85%, even more often more than about 90%, and most often at least about 99%. Preferably, the microarray has binding sites for genes relevant to the action of a drug of interest or in a biological pathway of interest. A "gene" is identified as an open reading frame (ORF) of preferably at least 50, 75, or 99 amino acids from which a messenger RNA is transcribed in the organism (e.g., if a single cell) or in some cell in a multicellular organism. The number of genes in a genome can be estimated from the number of mRNAs expressed by the organism, or by extrapolation from a well-characterized portion of the genome. When the genome of the organism of interest has been sequenced, the number of ORFs can be determined and mRNA coding regions identified by analysis of the DNA sequence. For example, the *Saccharomyces cerevisiae* genome has been completely sequenced and is reported to have approximately 6275 open reading frames (ORFs) longer than 99 amino acids. Analysis of these ORFs indicates that there are 5885 ORFs that are likely to specify protein products (Goffeau et al., 1996, Life with 6000 genes, Science 274:546–567, which is incorporated by reference in its entirety for all purposes). In contrast, the human genome is estimated to contain approximately 105 genes.

Preparing Nucleic Acids for Microarrays

As noted above, the "binding site" to which a particular cognate cDNA specifically hybridizes is usually a nucleic acid or nucleic acid analogue attached at that binding site. In one embodiment, the binding sites of the microarray are DNA polynucleotides corresponding to at least a portion of each gene in an organism's genome. These DNAs can be obtained by, e.g., polymerase chain reaction (PCR) amplification of gene segments from genomic DNA, cDNA (e.g., by RT-PCR), or cloned sequences. PCR primers are chosen, based on the known sequence of the genes or cDNA, that result in amplification of unique fragments (i.e. fragments that do not share more than 10 bases of contiguous identical sequence with any other fragment on the microarray). Computer programs are useful in the design of primers with the required specificity and optimal amplification properties. See, e.g., Oligo version 5.0 (National Biosciences). In the case of binding sites corresponding to very long genes, it will sometimes be desirable to amplify segments near the 3' end of the gene so that when oligo-dT primed cDNA probes are hybridized to the microarray, less-than-full length probes will bind efficiently. Typically each gene fragment on the microarray will be between about 50 bp and about 2000 bp, more typically between about 100 bp and about 1000 bp, and usually between about 300 bp and about 800 bp in length. PCR methods are well known and are described, for example, in Innis et al. eds., 1990, *PCR Protocols: A Guide to Methods and Applications*, Academic Press Inc. San Diego, Calif., which is incorporated by reference in its entirety for all purposes. It will be apparent that computer controlled robotic systems are useful for isolating and amplifying nucleic acids.

An alternative means for generating the nucleic acid for the microarray is by synthesis of synthetic polynucleotides or oligonucleotides, e.g., using N-phosphonate or phosphoramidite chemistries (Froehler et al., 1986, *Nucleic Acid Res* 14:5399–5407; McBride et al., 1983, *Tetrahedron Lett.* 24:245–248). Synthetic sequences are between about 15 and about 500 bases in length, more typically between about 20 and about 50 bases. In some embodiments, synthetic nucleic acids include non-natural bases, e.g., inosine. As noted above, nucleic acid analogues may be used as binding sites for hybridization. An example of a suitable nucleic acid analogue is peptide nucleic acid (see, e.g., Egholm et al., 1993, PNA hybridizes to complementary oligonucleotides obeying the Watson-Crick hydrogen-bonding rules, *Nature* 365:566–568; see also U.S. Pat. No. 5,539,083).

In an alternative embodiment, the binding (hybridization) sites are made from plasmid or phage clones of genes, cDNAs (e.g., expressed sequence tags), or inserts therefrom (Nguyen et al., 1995, Differential gene expression in the murine thymus assayed by quantitative hybridization of arrayed cDNA clones, *Genomics* 29:207–209). In yet another embodiment, the polynucleotide of the binding sites is RNA.

Attaching Nucleic Acids to the Solid Surface

The nucleic acid or analogue are attached to a solid support, which may be made from glass, plastic (e.g., polypropylene, nylon), polyacrylamide, nitrocellulose, or other materials. A preferred method for attaching the nucleic acids to a surface is by printing on glass plates, as is described generally by Schena et al., 1995, Quantitative monitoring of gene expression patterns with a complementary DNA microarray, *Science* 270:467–470. This method is especially useful for preparing microarrays of cDNA. See also DeRisi et al., 1996, Use of a cDNA microarray to analyze gene expression patterns in human cancer, *Nature Genetics* 14:457–460; Shalon et al., 1996, A DNA microarray system for analyzing complex DNA samples using two-color fluorescent probe hybridization, *Genome Res.* 6:639–645; and Schena et al., 1995, Parallel human genome analysis; microarray-based expression of 1000 genes, *Proc. Natl. Acad. Sci. USA* 93:10539–11286. Each of the aforementioned articles is incorporated by reference in its entirety for all purposes.

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Light-directed spatially addressable parallel chemical synthesis, *Science* 251:767–773; Pease et al., 1994, Light-directed oligonucleotide arrays for rapid DNA sequence analysis, *Proc. Natl. Acad. Sci. USA* 91:5022–5026; Lockhart et al., 1996, Expression monitoring by hybridization to high-density oligonucleotide arrays, *Nature Biotech* 14:1675; U.S. Pat. Nos. 5,578,832; 5,556,752; and 5,510,270, each of which is incorporated by reference in its entirety for all purposes) or other methods for rapid synthesis and deposition of defined oligonucleotides (Blanchard et al., 1996, High-Density Oligonucleotide arrays, *Biosensors & Bicelectronics* 11: 687–90). When these methods are used, oligonucleotides (e.g., 20-mers) of known sequence are synthesized directly on a surface such as a derivatized glass slide. Usually, the array produced is redundant, with several oligonucleotide molecules per RNA. Oligonucleotide probes can be chosen to detect alternatively spliced mRNAs. Another preferred method of making microarrays is by use of an inkjet printing process to synthesize oligonucleotides directly on a solid phase, as described, e.g., in copending U.S. patent application Ser. No. 09/008,120 filed on Jan. 16, 1998 by Blanchard entitled "Chemical Synthesis Using Solvent Microdroplets", which is incorporated by reference herein in its entirety.

Other methods for making microarrays, e.g., by masking (Maskos and Southern, 1992, *Nuc. Acids Res.* 20:1679–1684), may also be used. In principal, any type of array, for example, dot blots on a nylon hybridization membrane (see Sambrook et al., Molecular Cloning—A Laboratory Manual (2nd Ed.), Vol. 1–3, Cold Spring Harbor Laboratory, Cold Spring Harbor, N.Y., 1989, which is incorporated in its entirety for all purposes), could be used, although, as will be recognized by those of skill in the art, very small arrays will be preferred because hybridization volumes will be smaller.

Generating Labeled Probes

Methods for preparing total and poly(A)$^+$ RNA are well known and are described generally in Sambrook et al., supra. In one embodiment, RNA is extracted from cells of the various types of interest in this invention using guanidinium thiocyanate lysis followed by CsCl centrifugation (Chirgwin et al., 1979, *Biochemistry* 18:5294–5299). Poly(A)$^+$ RNA is selected by selection with oligo-dT cellulose (see Sambrook et al., supra). Cells of interest include wild-type cells, drug-exposed wild-type cells, modified cells, and drug-exposed modified cells.

Labeled cDNA is prepared from mRNA by oligo dT-primed or random-primed reverse transcription, both of which are well known in the art (see e.g., Klug and Berger, 1987, *Methods Enzymol.* 152:316–325). Reverse transcription may be carried out in the presence of a dNTP conjugated to a detectable label, most preferably a fluorescently labeled dNTP. Alternatively, isolated mRNA can be converted to labeled antisense RNA synthesized by in vitro transcription of double-stranded cDNA in the presence of labeled dNTPs (Lockhart et al., 1996, Expression monitoring by hybridization to high-density oligonucleotide arrays, *Nature Biotech.* 14:1675, which is incorporated by reference in its entirety for all purposes). In alternative embodiments, the cDNA or RNA probe can be synthesized in the absence of detectable label and may be labeled subsequently, e.g., by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent.

When fluorescently-labeled probes are used, many suitable fluorophores are known, including fluorescein, lissamine, phycoerythrin, rhodamine (Perkin Elmer Cetus), Cy2, Cy3, Cy3.5, Cy5, Cy5.5, Cy7, FluorX (Amersham) and others (see, e.g., Kricka, 1992, Nonisotopic DNA Probe Techniques, Academic Press San Diego, Calif.). It will be appreciated that pairs of fluorophores are chosen that have distinct emission spectra so that they can be easily distinguished.

In another embodiment, a label other than a fluorescent label is used. For example, a radioactive label, or a pair of radioactive labels with distinct emission spectra, can be used (see Zhao et al., 1995, High density cDNA filter analysis: a novel approach for large-scale, quantitative analysis of gene expression, *Gene* 156:207; Pietu et al., 1996, Novel gene transcripts preferentially expressed in human muscles revealed by quantitative hybridization of a high density cDNA array, *Genome Res.* 6:492). However, because of scattering of radioactive particles, and the consequent requirement for widely spaced binding sites, use of radioisotopes is a less-preferred embodiment.

In one embodiment, labeled cDNA is synthesized by incubating a mixture containing 0.5 mM dGTP, DATP and dCTP plus 0.1 mM dTTP plus fluorescent deoxyribonucleotides (e.g., 0.1 mM Rhodamine 110 UTP (Perken Elmer Cetus) or 0.1 mM Cy3 dUTP (Amersham)) with reverse transcriptase (e.g., SuperScript™ II, LTI Inc.) at 42° C. for 60 min.

Hybridization to Microarrays

Nucleic acid hybridization and wash conditions are chosen so that the probe "specifically binds" or "specifically hybridizes" to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al., supra, and Chee et al., supra).

Optimal hybridization conditions will depend on the length (e.g., oligomer versus polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., 1987, Current Protocols in Molecular Biology, Greene Publishing and Wiley-Interscience, New York, which is incorporated in its entirety for all purposes. When the cDNA microarrays of Schena et al. are used, typical hybridization conditions are hybridization in 5× SSC plus 0.2% SDS at 65° C. for 4 hours followed by washes at 25° C. in low stringency wash buffer (1× SSC plus 0.2% SDS) followed by 10 minutes at 25° C. in high stringency wash buffer (0.1×SSC plus 0.2% SDS) (Shena et al., 1996, *Proc. Natl. Acad. Sci. USA,* 93:10614). Useful hybridization conditions are also provided in, e.g., Tijessen, 1993, *Hybridization With Nucleic Acid Probes,* Elsevier Science Publishers B.V. and Kricka, 1992, Nonisotopic DNA Probe Techniques, Academic Press San Diego, Calif.

Signal Detection and Data Analysis

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, A DNA microarray system for analyzing complex DNA samples using two-color fluorescent probe hybridization, *Genome Research* 6:639–645, which is incorporated by reference in its entirety for all purposes). In a preferred embodiment, the arrays are scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., 1996, *Genome Res.* 6:639–645 and in other references cited herein. Alternatively, the fiber-optic bundle described by Ferguson et al., 1996, *Nature Biotech.* 14:1681–1684, may be used to monitor mRNA abundance levels at a large number of sites simultaneously.

Signals are recorded and, in a preferred embodiment, analyzed by computer, e.g., using a 12 bit analog to digital board. In one embodiment the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA in two cells or cell lines is scored as a perturbation and its magnitude determined (i.e., the abundance is different in the two sources of mRNA tested), or as not perturbed (i.e., the relative abundance is the same). As used herein, a difference between the two sources of RNA of at least a factor of about 25% (RNA from one source is 25% more abundant in one source than the other source), more usually about 50%, even more often by a factor of about 2 (twice as abundant), 3 (three times as abundant) or 5 (five times as abundant) is scored as a perturbation. Present detection methods allow reliable detection of difference of an order of about 3-fold to about 5-fold, but more sensitive methods are expected to be developed.

Preferably, in addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

Measurement of Response Profiles

In one embodiment of the invention, transcript arrays reflecting the transcriptional state of a cell of interest are made by hybridizing a mixture of two differently labeled probes each corresponding (i.e., complementary) to the mRNA of a different cell of interest, to the microarray. According to the present invention, the two cells are of the same type, i.e., of the same species and strain, but may differ genetically at a small number (e.g., one, two, three, or five, preferably one) of loci. Alternatively, they are isogeneic and differ in their environmental history (e.g., exposed to a drug versus not exposed).

In order to measure response profiles, cells are prepared or grown in the presence of graded perturbations to a the activity of a protein of interest. The cells exposed to the perturbation and cells not exposed to the perturbation are used to construct transcript arrays, which are measured to find the mRNAs with modified expression and the degree of modification due to exposure to the drug. Thereby, the response profile is obtained.

The density of levels of the graded perturbation control parameter is governed by the sharpness and structure in the individual gene responses—the steeper the steepest part of the response, the denser the levels needed to properly resolve the response. This exemplary density is approximately indicated by the example of FIG. 2. There, six exposures to methotrexate over a hundred-fold range of concentrations was just sufficient to resolve the gene expression responses. However, more exposures are preferably to more finely represent this pathway.

Further, it is preferable, in order to reduce experimental error, to reverse the fluorescent labels in two-color differential hybridization experiments to reduce biases peculiar to individual genes or array spot locations. In other words, it is preferable to first measure gene expression with one labeling (e.g., labeling perturbed cells with a first fluorochrome and unperturbed cells with a second fluorochrome) of the mRNA from the two cells being measured, and then to measure gene expression from the two cells with reversed labeling (e.g., labeling perturbed cells with the second fluorochrome and unperturbed cells with the first fluorochrome). Multiple measurements over exposure levels and perturbation control parameter levels provide additional experimental error control. With adequate sampling a trade-off may be made when choosing the width of the spline function S used to interpolate response data between averaging of errors and loss of structure in the response functions. Approximately ten measurements over drug exposure and perturbation control parameter intervals, repeated with reversal of the fluorescent labels, which together require approximately 20 hybridization experiments per drug response or perturbation response, achieve reliable identification of pathways and their member genes and proteins.

Measurement of Diagnostic Profiles

Diagnostic profiles may be obtained for any cell type in which it may be desirable to analyze the activity level of some protein. Preferably, the protein must be one for which perturbation response profiles are either already available, or can be generated. Cells for which it may be desirable to obtain diagnostic profiles include, for example, cells suspected of having genetic mutations or polymorphisms which disrupt protein activity levels, as well as cells which have been exposed to a drug or a combination of drugs which may affect protein activity levels.

To measure diagnostic profiles of cells suspected of having genetic mutations or polymorphisms which affect protein activity, cells suspected of having a genetic mutation or polymorphism and wild type cells of the same cell type are used to construct transcript arrays, which are measured to find the mRNAs with altered expression due to the genetic mutation or polymorphism. Thereby, the diagnostic profile is obtained.

To measure diagnostic profiles of cells exposed to a drug, the cells are exposed to some level of the drug of interest, preferably a level corresponding to clinical dosages of the drug. When the cells are grown in vitro, the drug is usually added to their nutrient medium. In the case of yeast, it is preferable to harvest the yeast in early log phase, since expression patterns are relatively insensitive to time of harvest at that time. The drug is added is a graded amount that depends on the particular characteristics of the drug, but usually will be between about 1 ng/ml and 100 mg/ml. In some cases a drug will be solubilized in a solvent such as DMSO.

The cells exposed to the drug and cells not exposed to the drug are used to construct transcript arrays, which are measured to find the mRNAs with altered expression due to exposure to the drug. Thereby, the drug response is obtained.

Similarly for measurements of response profiles, it is preferable also for diagnostic profiles, in the case of two-color differential hybridization, to measure also with reversed labeling.

Other Methods of Transcriptional State Measurement

The transcriptional state of a cell may be measured by other gene expression technologies known in the art. Several such technologies produce pools of restriction fragments of limited complexity for electrophoretic analysis, such as methods combining double restriction enzyme digestion with phasing primers (see, e.g., European Patent 0 534858 A1, filed Sep. 24, 1992, by Zabeau et al.), or methods selecting restriction fragments with sites closest to a defined mRNA end (see, e.g., Prashar et al., 1996, Proc. Natl. Acad. Sci. USA 93:659–663). Other methods statistically sample cDNA pools, such as by sequencing sufficient bases (e.g., 20–50 bases) in each of multiple cDNAs to identify each cDNA, or by sequencing short tags (e.g., 9–10 bases) which are generated at known positions relative to a defined mRNA end (see, e.g., Velculescu, 1995, Science 270:484–487).

5.5.2. Measurement of other Aspects of Biological State

In various embodiments of the present invention, aspects of the biological state other than the transcriptional state, such as the translational state, the activity state, or mixed aspects can be measured in order to obtain drug and pathway responses. Details of these embodiments are described in this section.

Embodiments Based on Translational State Measurements

Measurement of the translational state may be performed according to several methods. For example, whole genome monitoring of protein (i.e., the "proteome," Goffeau et al., supra) can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a drug of interest. Methods for making monoclonal antibodies are well known (see, e.g., Harlow and Lane, 1988, *Antibodies: A Laboratory Manual*, Cold Spring Harbor, N.Y., which is incorporated in its entirety for all purposes). In a preferred embodiment, monoclonal antibodies are raised against synthetic peptide fragments designed based on genomic sequence of the cell. With such an antibody array, proteins from the cell are contacted to the array. and their binding is assayed with assays known in the art.

Alternatively, proteins can be separated by two-dimensional gel electrophoresis systems Two-dimensional gel electrophoresis is well-known in the art and typically involves iso-electric focusing along a first dimension followed by SDS-PAGE electrophoresis along a second dimension. See, e.g., Hames et al, 1990, *Gel Electrophoresis of Proteins: A Practical Approach*, IRL Press, New York; Shevchenko et al., 1996, *Proc. Nat'l Acad. Sci. USA* 93:1440-1445; Sagliocco et al., 1996, *Yeast* 12:1519–1533; Lander, 1996, *Science* 274:536–539. The resulting electropherograms can be analyzed by numerous techniques, including mass spectrometric techniques, western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or overexpression of a specific gene.

Embodiments Based on Other Aspects of the Biological State

Although monitoring cellular constituents other than mRNA abundances currently presents certain technical difficulties not encountered in monitoring mRNAs, it will be apparent to those of skill in the art that the use of methods of this invention, including application of various known methods of pathway perturbation, are applicable to any cellular constituent that can be monitored.

In particular, where activities of proteins relevant to the characterization of drug action can be measured, embodiments of this invention can be based on such measurements. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known and measured, the changes in protein activities form the response data analyzed by the foregoing methods of this invention.

In alternative and non-limiting embodiments, response data may be formed of mixed aspects of the biological state of a cell. Response data can be constructed from, e.g., changes in certain mRNA abundances, changes in certain protein abundances, and changes in certain protein activities.

5.6. Applications of the Invention

The present invention has numerous applications in the field of biology and medicine, some of which are presented herein. Many other applications will be apparent to those skilled in the art, and are intended to be comprehended within the scope of the accompanying claims.

In one application, the present invention provides a method for identifying individuals who have mutations and/or polymorphisms that disrupt the function of important genes. As noted supra, there are numerous cancer susceptibility genes, numerous genes that determine metabolism of drugs, and genes that determine the presence of numerous disease states which, if altered in one of the two alleles, provide an increased risk for a large set of health related problems.

However, it is often not possible to determine the defective genotype in the heterozygous case since the wild type copy of the gene will also be present. Also, the exact sequence of the mutated copy will not generally be known. The method of the present invention provides this information.

For example, provided with a susceptibility gene that is associated with a particular disease state, and which is also associated with a particular gene product, preferably a particular protein, the methods of the present invention can be applied to identify individuals having mutations and/or polymorphisms of that gene which affect the activity level of its associated gene product, thereby identifying individuals having an increased susceptibility to the disease state associated with mutations and/or polymorphisms of that particular gene.

Figure 3:
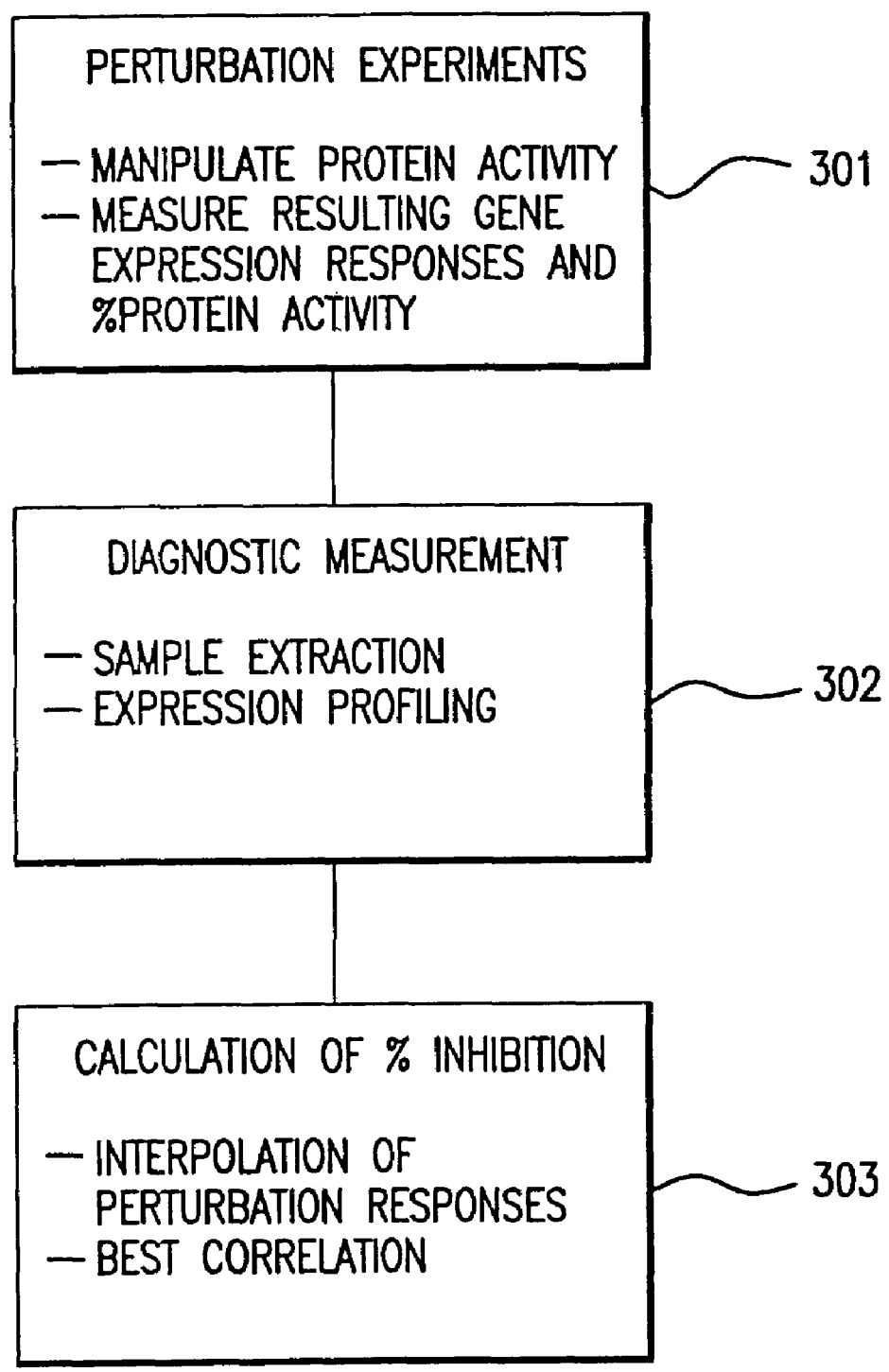
FIG. 3 illustrates a flow chart of an embodiment of the methods of the present invention.

This application can be achieved by direct employment of the methods generally described in Section 5.2, and specifically in Section 5.3, below, especially with reference to FIG. 3. Accordingly, in one aspect, this is achieved by: (i) obtaining a diagnostic profile by measuring abundances of cellular constituents in a cell, or more typically a sample of cells (e.g., a cell culture) obtained from an individual suspected of having genetic mutations and/or polymorphisms which disrupt the activity of a particular protein; (ii) obtaining response curves for the particular protein whose activity is disrupted by genetic mutations or polymorphisms by measuring abundances of cellular constituent in a cell in response to known, controlled perturbations of the particular protein to obtain response profiles, and interpolating the response profiles thus obtained; and (iii) determining the protein activity level at which the response profile extracted from the response curves best fits the measured diagnostic profile according to some objective measure. An individual is identified as having a genetic mutation or polymorphism which disrupts the activity of a particular protein if the protein activity level determined in step (iii) is different from that of a wild type cell.

More generally, the methods of the invention can be used to identify individuals having genetic mutations or polymorphisms of one or more genes which alter the activity of their corresponding gene products. In such embodiments, perturbation response curves are obtained, individually, for each gene product disrupted by genetic mutation(s) and/or polymorphism(s) in its corresponding gene. The diagnostic profile is then compared to a combination of response profiles extracted at activity levels for each protein, as described in Section 5.3, below.

The above method can be used to identify individuals having heterozygous mutations (i.e., mutations in only one of the two alleles of a gene) as well as haplo-insufficient individuals. Further, it is not necessary to know the sequence of the mutated gene itself to identify individuals having a mutation by the above method.

In certain instances, it may not be practical or possible to obtain response curves for a protein according to the methods discussed in Section 5.4, above. For example, the protein or gene product encoded by a susceptibility gene may not have been identified, or may not be characterized so that its activity cannot be perturbed at known, controlled activity levels to generate response profiles. In such instances, it is possible to analyze the expression profiles from a series of individuals who have known, heterozygous mutations in order to identify a response profile that can be used to identify uncharacterized individuals suspected of carrying similar mutations.

Such uncharacterized individuals can be identified by comparing the diagnostic profile obtained according to the above method with the response profile identified by analyzing expression profiles obtained from individuals who have known, heterozygous mutations, as well as with a response profile identified by analyzing expression profiles obtained from wild type individuals who do not have a heterozygous mutation and determining which response profile best fits the diagnostic profile according to some objective measure. An individual is thereby characterized as having the same genetic mutations if the fit of the perturbation profile to the individual's diagnostic profile has a suitable statistical significance, derived via randomization of the cell constituent index as described in Section 5.3.2, above. Preferably, the fit has at least the standard 95% probability threshold commonly used in medical science.

In another application, the methods of the present invention can be used to identify the activity of drugs in vivo. As used herein, drugs may be compounds of any degree of complexity that perturb a biological system, whether by known or unknown mechanisms and whether or not they are used therapeutically. Drugs thus include: typical small molecules of research or therapeutic interest; naturally-occurring factors, such as endocrine, paracrine, or autocrine factors, or factors interacting with cell receptors of all types; intracellular factors, such as elements of intracellular signaling pathways; factors isolated from other natural sources; and so forth. Most drugs exert their affects by interacting with a protein. Drugs may thereby either stimulate or increase activity levels of a protein, or inhibit or decrease activity levels of a protein. Drugs that increase protein activity levels are called herein "activating drugs", while drugs that decrease protein activity levels are called herein "inhibiting drugs".

Thus the activity of drugs can be assayed in vivo by using the methods of the present invention to determine the activity levels of one or more proteins that interact with one or more drugs of interest. In one aspect, this is achieved by (i) obtaining a diagnostic profile by measuring abundances of cellular constituents in a cell treated with a particular drug or drugs of interest; (ii) obtaining response curves for each particular protein which interacts with the drug(s) of interest by measuring abundances of cellular constituents in a cell in response to known, controlled perturbations of the protein to obtain response profiles, and interpolating the response profiles thus obtained; and (iii) determining the protein activity levels at which a combination of the response profiles extracted for each protein from the response curves best fits the measured diagnostic profile according to some objective measure. The protein activity levels thus determined are then a measure of activity of the drug or drugs of interest. Specifically, protein activity levels greater than those of wild type cells (i.e., greater than 100% %-protein activity) indicate drug activity for activating drugs, while protein activity levels that are less than those of wild type cells (i.e., less than 100% %-protein activity) indicate drug activity for inhibiting drugs. In general, higher levels of protein activity indicate higher drug activity for activating drugs, whereas lower levels of protein activity indicate higher levels of drug activity in inhibiting drugs.

In certain preferred embodiments of these methods, the activity level of a protein or proteins affected by the drug is not determined per se, but is determined indirectly, e.g., by calibrating perturbation response profiles to one or more clinical effects of the drug or drugs. Returning again to the exemplary response profiles illustrated in FIG. 2, in one preferred embodiment the horizontal axis of such a plot may be calibrated and/or expressed in terms of the clinical or therapeutic effect of a drug or drug therapy for which such perturbation response profiles are obtained or provided. Patients who are on the drug therapy may then have their dosages personalized by adjusting the dose or dosages so that the degree of gene expression response matches that associated with a particular clinical effect (e.g., a particular level of clinical effect). Such calibration of the horizontal axis may be done, e.g., by using past treatment response (i.e., response profiles) of the patient undergoing therapy. Alternatively, such calibration may also be done by using treatment response (i.e., response profiles) from a different patient or patients. Preferably, the different patient or patients are analogous patients who, e.g., have a similar genetic background (i.e., are genetically similar) to the patient undergoing the therapy, and/or have a similar clinical response to the drug.

For instance, in one exemplary non-limiting embodiment, the drug therapy may comprise the administration of one or more cholesterol lowering drugs. In such embodiments, levels of clinical or therapeutic effect may comprise clinical measures (e.g., LDL levels or levels of some undesired side effect). By calibrating the horizontal axis of a collection of perturbation response profiles to such a clinical effect or effects, a desirable clinical effect can be readily achieved for a particular patient by adjusting the dose of the drug or drugs until the patient's cellular constituent profile (e.g., the patient's gene profile) matches the profile obtained in the calibrated response profiles at the desired level of clinical effect (i.e., at the position along the horizontal axis that corresponds to or is calibrated for the desired level of clinical effect). Although a certain level or levels of protein inhibition may, in fact, be achieved by the drug or drugs, such levels of protein activity are not measured per se. Indeed, in such clinical applications the actual level of inhibition is generally immaterial or not of interest since the actual effect of interest is the actual effectiveness of the drug as determined from other clinical measures.

Such methods may also be used to select an appropriate drug therapy for a patient by adjusting or determining the drug therapy administered to the patient so that the degree of gene expression response matches that associated with a particular clinical effect. In particular, the drug therapy administered to a patient will comprise a selection of one or more particular drugs and a selection of dosages at which each of the one or more particular drugs is administered. Thus, the drug therapy administered to a patient may be adjusted or determined, e.g., by adjusting or determining the one or more particular drugs to administer to that patient and/or adjusting or determining the dosages at which the one or more particular drugs are administered.

In such embodiments, perturbation response profiles are obtained for a plurality of drug therapies wherein the drug or drugs administered and/or the drug dosages are varied. By calibrating these perturbation response profiles to a clinical effect or effects, a desirable clinical effect can be readily achieved for a particular patient by adjusting the drug therapy until the patient's cellular constituent profile matches the profile obtained in the calibrated response profiles at the desired level of clinical effect.

6. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A computer system for determining a level of protein activity in a cell of a cell type comprising a processor and a memory coupled to said processor, said memory encoding one or more programs, said one or more programs causing said processor to perform a method comprising
   (i) receiving perturbation response profiles of said protein for said cell type, wherein each said perturbation response profile comprises measurements of a plurality of cellular constituents in a first cell of said cell type at one of a plurality of discrete levels of perturbation to said protein,
   (ii) interpolating measurements of each cellular constituent of said plurality in said perturbation response profiles over said plurality of discrete levels of said perturbation to obtain a perturbation response curve of measurements of said cellular constituent as a function of level of said perturbation to said protein so that an interpolated perturbation response profile comprising measurements of said plurality of cellular constituents may be extracted at any level over a range of levels of perturbation to said protein, and
   (iii) determining a level of perturbation to said protein at which similarity is greatest between a diagnostic profile and an interpolated perturbation response profile, said diagnostic profile comprising measurements of said plurality of cellular constituents in a second cell of said cell type, said interpolated perturbation response profile comprising measurements of said plurality of cellular constituents extracted for said determined level from said perturbation response curves;
wherein said determined level of perturbation to said protein represents said protein activity level in said cell type.

2. The computer system of claim 1 wherein determining the level of perturbation is achieved by a method comprising:
   (a) determining the value of a function of the difference between said diagnostic profile and an interpolated perturbation response profile extracted from said perturbation response curves for a level of perturbation to said protein; and
   (b) minimizing said determined value of said function by varying the level of perturbation to said protein to determine a level of perturbation that minimizes said determined value of said function.

3. The computer system of claim 1 wherein said diagnostic profile and said perturbation response profiles are made available in said memory.

4. The computer system of claim 3 wherein said programs cause said processor to perform said step of interpolating said perturbation response profiles.

5. The computer system of claim 2 wherein said function comprises a sum of the squares of differences of measurements in the diagnostic profile and measurements in the interpolated perturbation response profile extracted from said perturbation response curves.

6. The computer system of claim 1 wherein determining the level of perturbation is achieved by a method comprising:
  (a) determining the value of a function of the correlation between said diagnostic profile and an interpolated perturbation response profile extracted from said perturbation response curves for a level of perturbation to said protein; and
  (b) maximizing said determined value of said function by varying the level of perturbation to said protein to determine a level of perturbation that maximizes said determined value of said function.

7. The computer system of claim 2 wherein said minimizing comprises performing the Levenberg-Marquardt method.

8. A computer system for determining levels of activities of a plurality of proteins in a cell of a cell type comprising a processor and a memory coupled to said processor, said memory encoding one or more programs, said one or more programs causing said processor to perform a method comprising
  (i) receiving perturbation response profiles of each said protein for said cell type, wherein each said perturbation response profile comprises measurements of a plurality of cellular constituents in a first cell of said cell type at one of a plurality of discrete levels of perturbation to said protein,
  (ii) interpolating measurements of each cellular constituent of said plurality in said perturbation response profiles of each said protein over said plurality of discrete levels of said perturbation levels to obtain a perturbation response curve of measurements of said cellular constituent as a function of level of said perturbation to said protein so that an interpolated perturbation response profile comprising measurements of said plurality of cellular constituents may be extracted at any level over a range of levels of perturbation to said protein, and
  (iii) determining a level of perturbation to each said protein at which similarity is greatest between a diagnostic profile and a combination of interpolated perturbation response profiles, said diagnostic profile comprising measurements of said plurality of cellular constituents in a second cell of said cell type, each said interpolated perturbation response profile comprising measurements of said plurality of cellular constituents extracted for said determined level of perturbation to a protein in said plurality of proteins from said perturbation response curves,
wherein said determined level of perturbation to each said protein represents said activity level of each said protein in said cell type.

9. The computer system of claim 8 wherein said determining the level of perturbation is achieved by a method comprising:
  (a) determining the value of a function of the difference between said diagnostic profile and the combination of interpolated perturbation response profiles extracted from said perturbation response curves for said level of perturbation to each said protein; and
  (b) minimizing said determined value of said function by varying the level of perturbation to each said protein to determine the level of perturbation to each said protein that minimizes said determined value of said function.

10. A computer system for determining a level of activity of a biologically active cellular constituent of interest in a cell of a cell type comprising a processor and a memory coupled to said processor, said memory encoding one or more programs, said one or more programs causing said processor to perform a method comprising
  (i) receiving perturbation response profiles of the cellular constituent of interest for said cell type, wherein each said perturbation response profile comprises measurements of a plurality of cellular constituents in a first cell of said cell type at one of a plurality of discrete levels of perturbation to the cellular constituent of interest,
  (ii) interpolating measurements of each cellular constituent of said plurality in said perturbation response profiles over said plurality of discrete levels of said perturbation to obtain a perturbation response curve of measurements of said cellular constituent as a function of level of said perturbation to said protein so that an interpolated perturbation response profile comprising measurements of said plurality of cellular constituents may be extracted at any level over a range of levels of perturbation to the cellular constituent of interest, and
  (iii) determining a level of perturbation to the cellular constituent of interest at which similarity is greatest between a diagnostic profile and an interpolated perturbation response profile, said diagnostic profile comprising measurements of said plurality of cellular constituents in a second cell of said cell type, said interpolated perturbation response profile comprising measurements of said plurality of cellular constituents extracted for said determined level from said perturbation response curves,
wherein said determined level of perturbation to the cellular constituent of interest represents the activity level of said cellular constituent of interest in said cell type.

11. The computer system of claim 10, wherein determining the level of perturbation is achieved by a method comprising:
  (a) determining the value of a function of the difference between said diagnostic profile and an interpolated perturbation response profile extracted from said perturbation response curves for a level of perturbation to said cellular constituent of interest; and
  (b) minimizing said determined value of said function by varying the level of perturbation to said cellular constituent of interest to determine a level of perturbation that minimizes said determined value of said function.

12. A computer program product comprising a computer readable storage medium having a computer program mechanism encoded thereon, wherein said computer program mechanism may be loaded into the memory of a computer and cause said computer to carry out a method comprising:
  (i) receiving perturbation response profiles of a protein for a cell type, wherein each said perturbation response profile comprises measurements of a plurality of cellular constituents in a first cell of said cell type at one of a plurality of discrete levels of perturbation to said protein, (ii) interpolating measurements of each cellular constituent of said plurality in said perturbation response profiles over said plurality of discrete levels of said perturbation to obtain a perturbation response curve of measurements of said cellular constituent as a function of level of said perturbation to said protein so that an interpolated perturbation response profile comprising measurements of said plurality of cellular constituents may be extracted at any level over a range of levels of perturbation to said protein, and (iii) determining a level of perturbation to said protein at which similarity is greatest between a diagnostic profile and an interpolated perturbation response profile, said diagnostic profile comprising measurements of a plurality of cellular constituents in a second cell of said cell type, said interpolated perturbation response profile comprising measurements of said plurality of cellular constituents extracted for said determined level from said perturbation response curves, wherein said determined level of perturbation to said protein represents a level of activity of said protein in said cell type.

13. A computer program product comprising a computer readable storage medium having a computer program mechanism encoded thereon, wherein said computer program mechanism may be loaded into the memory of a computer and cause said computer to carry out a method comprising (i) receiving perturbation response profiles of a protein for a cell type, wherein each said perturbation response profile comprises measurements of a plurality of cellular constituents in a first cell of said cell type at one of a plurality of discrete levels of perturbation to said protein, (ii) interpolating measurements of each cellular constituent of said plurality in said perturbation response profiles over said plurality of discrete levels of said perturbation levels to obtain a perturbation response curve of measurements of said cellular constituent as a function of level of said perturbation to said protein so that an interpolated perturbation response profile comprising measurements of said plurality of cellular constituents may be extracted at any level over a range of levels of perturbation to said protein, and (iii) determining a level of perturbation to said protein at which similarity is greatest between a diagnostic profile and an interpolated perturbation response profile, said diagnostic profile comprising measurements of said plurality of cellular constituents in a cell treated with said drug; and said interpolated perturbation response profile comprising measurements of said plurality of cellular constituents extracted for said determined level from said perturbation response curves, and wherein said determined level of perturbation to said protein represents said protein activity level in said cell treated with said drug and said protein activity level is a measure of activity of said drug.

14. A computer program product comprising a computer readable storage medium having a computer program mechanism encoded thereon, wherein said computer program mechanism may be loaded into the memory of a computer and cause said computer to carry out a method comprising (i) receiving perturbation response profiles of a biologically active cellular constituent of interest for a cell type, wherein each said perturbation response profile comprises measurements of a plurality of cellular constituents in a first cell of said cell type at one of a plurality of discrete levels of perturbation to the cellular constituent of interest, (ii) interpolating measurements of each cellular constituent of said plurality in said perturbation response profiles over said plurality of discrete levels of said perturbation to obtain a perturbation response curve of measurements of said cellular constituent as a function of level of said perturbation to said cellular constituent of interest so that an interpolated perturbation response profile comprising measurements of said plurality of cellular constituents may be extracted at any level over a range of levels of perturbation to the cellular constituent of interest, and (iii) determining a level of perturbation to said cellular constituent of interest at which similarity is greatest between a diagnostic profile and an interpolated perturbation response profile, said diagnostic profile comprising measurements of a plurality of cellular constituents in a second cell of said cell type, said interpolated perturbation response profile comprising measurements of said plurality of cellular constituents extracted for said determined level from said perturbation response curves, wherein said determined level of perturbation to the cellular constituent of interest represents a level of activity of said cellular constituent of interest in said cell type.

* * * * *